(12) United States Patent
Taylor et al.

(10) Patent No.: US 11,751,027 B2
(45) Date of Patent: Sep. 5, 2023

(54) SYSTEM AND METHOD FOR DRIVING CONDITION DETECTION AND NOTIFICATION

(71) Applicant: Cyber Physical Systems LLC, Nashville, TN (US)

(72) Inventors: Melanie Taylor, Nashville, TN (US); Kyle Ducharme, Nashville, TN (US); Edmund J. Song, Nashville, TN (US)

(73) Assignee: Cyber Physical Systems, Inc., Nashville, TN (US)

( * ) Notice: Subject to any disclaimer, the term of this patent is extended or adjusted under 35 U.S.C. 154(b) by 137 days.

(21) Appl. No.: 17/447,398

(22) Filed: Sep. 10, 2021

(65) Prior Publication Data
US 2022/0174459 A1  Jun. 2, 2022

Related U.S. Application Data

(63) Continuation of application No. 16/339,715, filed as application No. PCT/US2017/055412 on Oct. 5, 2017, now Pat. No. 11,146,929.
(Continued)

(51) Int. Cl.
*H04W 4/44* (2018.01)
*H04W 4/029* (2018.01)
(Continued)

(52) U.S. Cl.
CPC .......... *H04W 4/44* (2018.02); *A61B 5/02055* (2013.01); *A61B 5/6893* (2013.01); *G07C 5/008* (2013.01);
(Continued)

(58) Field of Classification Search
CPC ......... H04W 4/44; H04W 4/029; H04W 4/90; A61B 5/02055; A61B 5/6893;
(Continued)

(56) References Cited

U.S. PATENT DOCUMENTS 5,574,427 A  11/1996 Cavallaro
6,504,471 B1  1/2003 Lam
(Continued)

FOREIGN PATENT DOCUMENTS

WO  WO 2018/067867 A1  4/2018

OTHER PUBLICATIONS

International Search Report and Written Opinion for PCT/US2017/055412 dated Feb. 6, 2018 (21 pages).
(Continued)

*Primary Examiner* — Eric Blount
(74) *Attorney, Agent, or Firm* — Nixon Peabody LLP

(57) ABSTRACT

A system for accident detection or detecting an unsafe driving condition in a vehicle including a device that measures and transmits at least one output signal; at least one remote device configured to receive, record, and/or display the at least one output signal from the device; a computing device configured to receive the at least one output signal from the device and display the at least one output signal in real-time; and a graphical user interface on the computing device that allows an emergency response professional to view and customize options for monitoring the at least one output signal, wherein the device, the at least one remote device, and the computing device are communicatively connected to each other via a communications network.

10 Claims, 11 Drawing Sheets

Related U.S. Application Data

(60) Provisional application No. 62/405,769, filed on Oct. 7, 2016.

(51) Int. Cl.
| | | |
|---|---|---|
| *H04W 4/90* | (2018.01) | |
| *A61B 5/0205* | (2006.01) | |
| *A61B 5/00* | (2006.01) | |
| *G07C 5/00* | (2006.01) | |
| *G07C 5/08* | (2006.01) | |
| *A61B 5/021* | (2006.01) | |
| *A61B 5/024* | (2006.01) | |
| *A61B 5/0533* | (2021.01) | |
| *A61B 5/08* | (2006.01) | |
| *A61B 5/145* | (2006.01) | |
| *A61B 5/1455* | (2006.01) | |
| *A61B 5/20* | (2006.01) | |
| *A61B 10/00* | (2006.01) | |
| *A61B 5/318* | (2021.01) | |

(52) U.S. Cl.
CPC ............ *G07C 5/08* (2013.01); *G07C 5/0825* (2013.01); *H04W 4/029* (2018.02); *H04W 4/90* (2018.02); *A61B 5/021* (2013.01); *A61B 5/02405* (2013.01); *A61B 5/0533* (2013.01); *A61B 5/0816* (2013.01); *A61B 5/14532* (2013.01); *A61B 5/14551* (2013.01); *A61B 5/20* (2013.01); *A61B 5/318* (2021.01); *A61B 2010/0009* (2013.01); *A61B 2560/0257* (2013.01)

(58) Field of Classification Search
CPC ... A61B 5/021; A61B 5/02405; A61B 5/0533; A61B 5/0816; A61B 5/14532; A61B 5/14551; A61B 5/20; A61B 5/318; A61B 2010/0009; A61B 2560/0257; G07C 5/008; G07C 5/08; G07C 5/0825

USPC ........................................................ 340/442

See application file for complete search history.

(56) References Cited

U.S. PATENT DOCUMENTS

| | | |
|---|---|---|
| 6,868,718 B1 | 3/2005 | Hui |
| 6,927,675 B2 | 8/2005 | Losee |
| 8,907,772 B1 | 12/2014 | Green |
| 9,111,316 B2 | 8/2015 | Fernandes |
| 9,792,807 B2 | 10/2017 | Benoit |
| 9,813,535 B2 | 11/2017 | Benoit |
| 9,824,064 B2 | 11/2017 | Lavie |
| 2005/0131597 A1 | 6/2005 | Raz |
| 2005/0156715 A1* | 7/2005 | Zou .......................... B60R 25/33 340/8.1 |
| 2005/0264404 A1 | 12/2005 | Franczyk |
| 2007/0075919 A1 | 4/2007 | Breed |
| 2007/0099163 A1* | 5/2007 | Tseng ....................... G09B 5/00 434/350 |
| 2007/0142986 A1* | 6/2007 | Alaous ................. G07C 5/0858 701/33.4 |
| 2008/0036580 A1 | 2/2008 | Breed |
| 2009/0085728 A1 | 4/2009 | Catten |
| 2011/0181443 A1 | 7/2011 | Gutierrez |
| 2011/0295446 A1 | 12/2011 | Basir |
| 2012/0044063 A1 | 2/2012 | McClellan |
| 2012/0073892 A1 | 3/2012 | Hunter |
| 2013/0006469 A1 | 1/2013 | Green |
| 2014/0274018 A1 | 9/2014 | Miller |

OTHER PUBLICATIONS

Extended European Search Report in International Application No. PCT/US2017/055412, dated Apr. 24, 2020 (8 pages).

\* cited by examiner

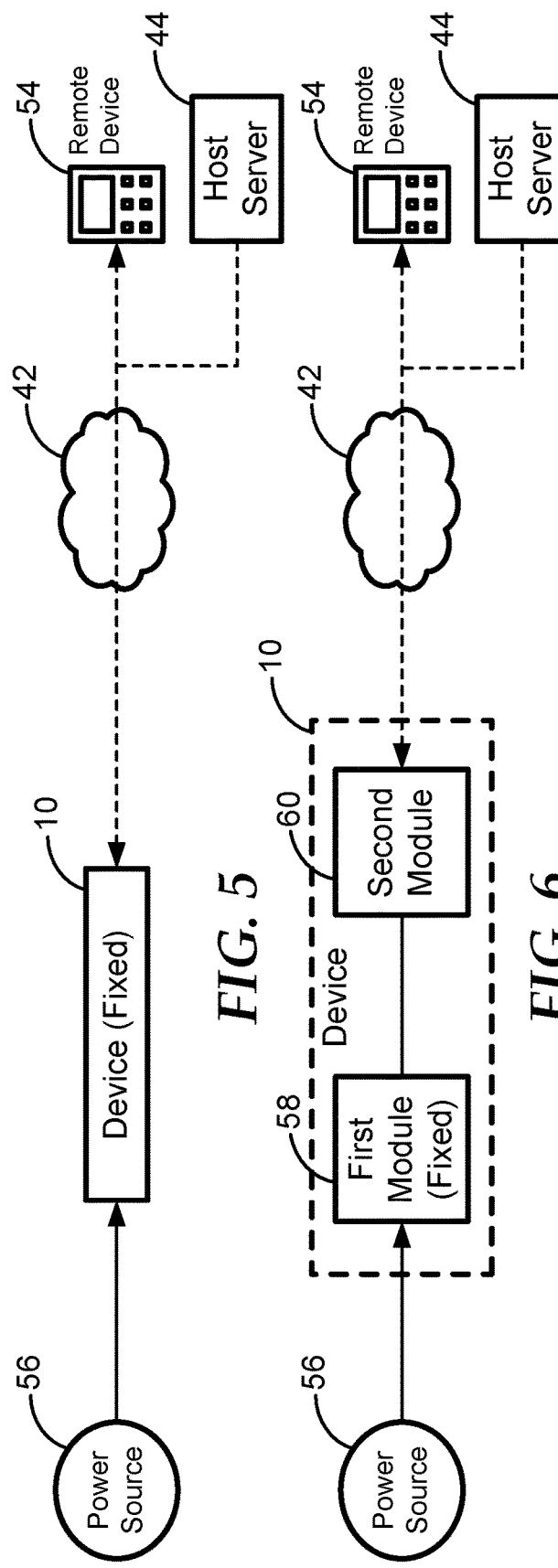
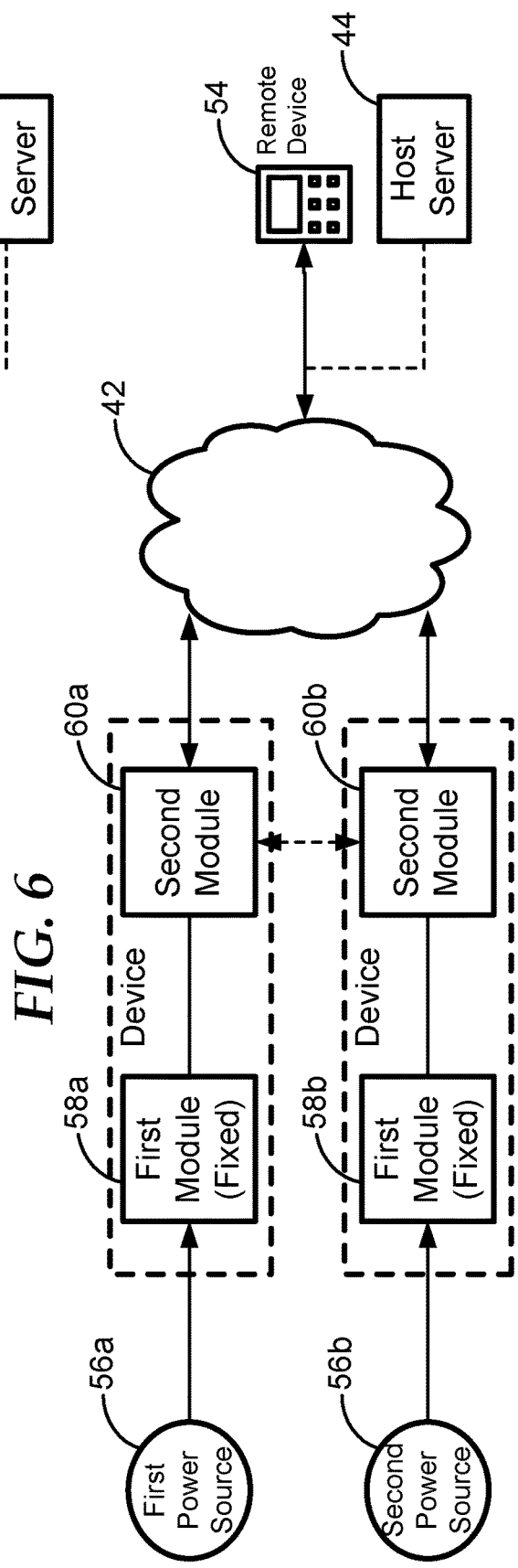

SYSTEM AND METHOD FOR DRIVING CONDITION DETECTION AND NOTIFICATION

CROSS-REFERENCE TO RELATED APPLICATIONS

This application is a continuation of U.S. application Ser. No. 16/339,715 filed on Apr. 4, 2019, which is a National Phase of International Application No. PCT/US2017/055412 filed on Oct. 5, 2017, which designated the U.S. and that International Application was published under PCT Article 21(2) in English, which also includes a claim of priority under 35 U.S.C. § 119(e) to U.S. provisional patent application No. 62/405,769 filed Oct. 7, 2016, each of which is hereby incorporated by reference herein in its entirety.

FIELD OF THE DISCLOSURE

The present disclosure relates generally to a device and system for determining the status of a vehicle, such as, for example, speed, location, accident, and the like, and transmitting associated data. More particularly, the present disclosure relates to a portable device for measuring data associated with vehicle movement and position, determining an unsafe driving status possibly associated with speeding, unstable driving conditions, an accident or other notable event, and transmitting data and/or alerts based on the determined status and/or measured data.

BACKGROUND OF THE DISCLOSURE

Conventional vehicle status or accident detectors are often used to promote safer driving and to allow emergency response professionals to respond faster to accidents. These conventional detectors are often built into vehicles, therefore making it difficult to continuously measure vehicle status of users who may have multiple vehicles. Additionally, the existing conventional detectors often measure only a single parameter (e.g., speed), and are unable to measure multiple parameters at once to allow for an early detection of a potential vehicle or driver problems that may be indicated by abnormities in multiple parameters when they are analyzed together. Furthermore, the lack of portable and scalable vehicle status and accident detectors often leads to overuse of emergency responder resources (e.g., emergency response professionals' time) which can be better spent on e.g., responding to more urgent or dangerous accidents, and the like.

An unfulfilled need exists for a means to enable continuous monitoring of vehicle status and the driver in a portable, easy-to-use manner.

BRIEF SUMMARY OF THE DISCLOSURE

An aspect of the present disclosure provides a system for accident detection or detecting an unsafe driving condition in a vehicle including a device that measures and transmits at least one output signal; at least one remote device configured to receive, record, and/or display the at least one output signal from the device; a computing device configured to receive the at least one output signal from the device and display the at least one output signal in real-time; and a graphical user interface on the computing device that allows an emergency response professional to view and customize options for monitoring the at least one output signal, wherein the device, the at least one remote device, and the computing device are communicatively connected to each other via a communications network.

The system may further include a hosted server that is (i) configured to store and analyze the at least one output signal and (ii) connected to the device, the at least one remote device, and the computing device via the communications network.

The hosted server may be further configured to measure, store, and analyze a normal driving pattern associated with a certain driver and dynamically aggregate and analyze the normal driving pattern of the driver with at least one output to determine the unsafe driving condition or potential unsafe driving condition.

The device may be configured to send an alarm or an unsafe driving notification to the at least one remote device, the computing device, or the emergency response professional based on the unsafe driving condition or the potential unsafe driving condition.

The device may be configured to detect an accident based on the at least one output signal and send an accident alert to at least one of following: the device, the computing device, or the emergency services professional.

The emergency services professional may include an emergency call center, police, hospital, and/or fire department.

The least one output signal may be associated with at least one of: movement of the vehicle, rotational position of the vehicle, biometric information regarding passengers in the vehicle, and/or geographic location of the vehicle.

The device may include at least one of: a movement sensor, a position sensor, a communications device, a control unit, an image sensor, electronic nose, a driver vital sign detector, and/or the audio sensor.

The movement sensor may include at least one of accelerometer, gyroscope, and/or magnetometer.

The position sensor may include at least one of: global positioning system (GPS), GLONASS, BeiDou, Galileo, NAVIC, QZSS, DORIS, geo-satellite service (GSS), cellular location data detector, and/or wireless location triangulation device.

The communications device may include at least one of RF module or a cellular/wireless modem and is configured to transmit the at least one measured output to the at least one remote device and/or the computing device.

The image sensor may include any RGB, CCD, CMOS or FLIR, infrared, etc. image sensor that is configured to detect and convey an image to at least one of the at least one remote device and/or the computing device.

The driver vital sign detector may include at least one of: heart rate monitor, pulse oximeter, electrocardiogram (EKG) monitor, respiratory monitor, blood pressure monitor, blood glucose monitor, urine monitor, barometric sensor, and/or thermometer.

The driver vital sign detector may be configured to measure at least one of: heart rate, blood oxygen, respiratory rate, heart rhythm, blood pressure, or body temperature, blood glucose, heart rate variability, and/or galvanic skin response.

The electronic nose may be configured to detect an odor, substance, or presence of a molecule in the vehicle.

The communications device may be configured to send an alarm of an unsafe driving notification to the at least one remote device, the computing device, software platform, operator console, or the emergency response professional if the at least one measured output passes a predetermined or preprogrammed value in the system.

The predetermined or the preprogrammed criteria may include at least one of: movement of the vehicle, unsafe driving parameters, predetermined speed limit associated with certain geographical area, or combination thereof.

The communications device may be configured to send an alarm or an unsafe driving notification to the at least one remote device, the computing device, or the emergency response professional if the odor, substance, or molecule passes a predetermined or a preprogrammed criteria in the system.

The predetermined or the preprogrammed criteria may include at least one of: carbon monoxide (CO), carbon dioxide (CO2), alcohol, cannabis, and/or any other chemical measurements.

The system may be configured to send an action signal to the vehicle if the odor passes the predetermined or preprogrammed criteria. The odor may include indicators of smoke, chemical, and the like.

The action signal may include locking the vehicle, turning on stop or head lights; applying emergency brakes, calling the emergency response professionals, applying a honk, applying an emergency headlight, and any combinations thereof.

The audio sensor may include a microphone. The audio sensor may be configured to detect an audio signal that signals danger and upon such detection, the communications device may be configured to transmit the audio signal to the emergency professional service professional. The audio signal may include any message associated with the audio signal, such as, for example, pitch, quality, loudness, and the like. The audio signal may be sent in a file format, such as, for example, way, flac, aac, aiff, way, mp3, 3ga, cda, opus, amr, mp4a, and the like. The audio signal may include a safe word, a scream, sound signature, and any other preprogrammed sound signal. The audio signal may be analyzed to detect an event, such as, for example, an accident, based on preprogrammed or predetermined sound profile in the device. Based on the audio signal, the device may automatically call for the emergency services professional.

The device may be configured to measure the at least one output signal as raw analog data and transmit the raw analog data to the at least one remote device.

The at least one remote device may be configured to convert the raw analog data into digital data to be transmitted to the computing device.

The at least one remote device may be configured to measure the at least one output signal as raw analog data and transmit the raw analog data to the computing device.

The computing device may be configured to convert the raw analog data into digital data.

The at least one remote device or the computing device may be configured to analyze the at least output signal of the vehicle to check for any anomalies for the vehicle that are preprogrammed into the system by the emergency response professional, a user, and/or the driver.

The at least one remote device may configured to display the at least one output signal to a verified user or an authorized user.

The graphical user interface may be configured to allow the emergency response professional or the driver to (i) set a range of acceptable measurements for the at least one output signal for each driver wherein an alarm or unsafe driving notification would be triggered if the at least one output signal falls outside the range of acceptable measurements; and/or (ii) set an automatic recourse if the at least one output signal falls outside the range of acceptable measurements.

The at least one remote device may include a computer readable code that is configured to analyze the at least one output signal of the vehicle or the driver.

The computer readable program code may be further configured to determine an acceptable range of the at least one output signal for each vehicle of driver based on an aggregate data of the at least one vital sign of each vehicle over a predetermined time period and trigger an alarm or unsafe driving notification if the at least one output signal falls outside the acceptable range.

The devices may include an identification unit that is configured to identify the driver and request the driver's normal driving patterns from the hosted server.

The identification unit may be further configured to identify the driver based on the driver's fingerprint, palm veins, face recognition, DNA, palm print, hand geometry, iris recognition, retina, scent, or any combination thereof.

The at least one remote device may include a position sensor which is configured to (i) detect a position of the at least one remote device and (ii) confirm that a driver is driving the vehicle based on simultaneous movement of the remote device and the vehicle.

The at least one remote device may include an identification verification unit that is configured to verify that the driver of the vehicle is also a user of the at least one remote device.

The at least one remote device may be configured to determine whether a user activity in combination with one or more running application is potentially dangerous by comparing the user activity in combination with one or more running applications to a predetermined criteria stored in the at least one remote device.

The predetermined criteria may include detection of simultaneous movement of the vehicle and the at least one remote device.

The at least one remote device may be configured to block one or more running applications upon determination that the user activity in combination with one or more running application is potentially dangerous.

The at least one remote device may be configured to block one or more running applications upon detection of simultaneous movement of the vehicle and the at least one remote device.

The device, the at least one remote device, and the computing device may be configured to be connected to an on-board diagnostics (OBD) system of the vehicle, or similar car telematics connection system of the vehicle.

The device, the at least one remote device, and the computing device are configured to pull OBD data from the OBD system and analyze the OBD data with the at least one output signal to determine a dangerous driving condition or an accident.

The device, the at least one remote device, and the computing device may be configured to send an action signal to the vehicle upon detection of the dangerous driving condition or the accident.

The action signal may include locking the vehicle, turning on stop or head lights; applying emergency brakes, calling the emergency response professionals, applying a honk, applying an emergency headlight, or any combinations thereof.

An aspect of the present disclosure provides a system for use in geofencing a vehicle, the system including a device that measures and transmits at least one output signal; at least one remote device which is configured to receive, record, and/or display the at least one output signal from the device; a computing device which is configured to receive from the device the at least one output signal and display the at least one output signal in real-time; and a graphic user interface on the computing device that allows a system administrator to view and customize options for monitoring the at least one output signal, wherein the device, the at least one remote device, and the computing device are connected to each other via a communications network, and wherein the device, the least one remote device, and the computing device are configured to measure, store, and analyze position of the vehicle in relation to a preprogrammed geographical area.

The device may include a movement sensor, a position sensor, a communications device, a control unit, an image sensor, electronic nose, a driver vital sign detector, and/or the audio sensor.

The at least one output signal may include any measurements detected by the movement sensor, a position sensor, a communications device, a control unit, an image sensor, electronic nose, a driver vital sign detector, and/or the audio sensor.

The position sensor may be configured to detect when the vehicle is approaching the preprogrammed area and transmit the detection to the at least one remote device, the computing device, and/or the system administrator.

The device, the at least one remote device, and/or the computing device may include a computer and a computer readable storage medium tangibly embodying a computer readable program code having computer readable instructions which, when implemented, cause the computer to carry out the steps of: detecting the position of the vehicle in relation to the preprogrammed geographical area; transmitting the position of the vehicle to the system administrator; and carrying out a geo-fencing action based on the position of the vehicle.

The geo-fencing action may include: electronically issuing a speeding ticket to the vehicle or the driver of the vehicle, electronically issuing a fine or a toll fee to the vehicle or the driver of the vehicle, applying an interlock mechanism to the vehicle, or any of the combinations thereof.

The preprogrammed geographical area may include at least one of military system, a police checkpoint, a tolling booth, a chemical plant, and/or any other restricted geographical areas.

Another aspect of the present disclosure provides a system for use in generating a traffic monitoring subsystem, the system including a device that measures and transmits position of the vehicle; at least one remote device which is configured to receive, record, and/or display the real-time position from the device and any other third party sources; a computing device which is configured to receive from the device the position and display the real-time position; and a graphic user interface on the computing device that allows a system administrator to view and customize options for monitoring the real-time position, wherein the device, the at least one remote device, and the computing device are connected to each other via a communications network, and wherein the device, the least one remote device, and the computing device are configured to generate a traffic monitoring subsystem by dynamically aggregating the real-time position of the vehicle in relation to a plurality of geographical locations associated with a plurality of remote devices and a plurality of devices.

Each of the devices and the at least one remote device may include an identification unit to verify that movement of the device matches movement of the at least one remote device.

The third party sources may include google Map®, Bing® map, Apple® map, municipality map, or any combinations thereof.

In yet another aspect of the present disclosure, a device for automatically detecting unsafe driving practices and providing real-time driver feedback is provided. The device includes: a housing configured to be coupled to a power source of a vehicle, the housing being fixed relative to the vehicle when coupled thereto; a power supply in the housing and configured to receive power from the power source of the vehicle when the housing is coupled thereto; a movement sensor in the housing and configured to generate output signals associated with movement of the vehicle; a geo-location sensor in the housing and configured to generate output signals associated with a geo-location of the vehicle; a communications module in the housing and configured to send and receive data via a communications network; and a control unit in the housing and coupled to the power supply, the movement sensor, the position sensor, and the communications device, the control unit including a processor and a memory device storing program instructions therein when executed by the processor are configured to cause the control unit to: receive, from a hosted server, a driver's normal driving parameters via the communications device, the normal driving parameters including preprogrammed driving patterns of said driver, the driver's driving patterns associated with the predetermined speed limit settings, the driver's driving patterns associated with unsafe driving locations, and the driver's driving patterns associated historically with one or more of unsafe driving conditions and accidents, receive, from the hosted server, unsafe driving parameters via the communications device, the unsafe driving parameters including predetermined speed limit settings and unsafe driving locations, the unsafe driving locations associated with the predetermined speed limit settings and historically with one or more of unsafe driving conditions and accidents, determine a geo-location of the vehicle based on the geo-location sensor output signals, aggregate data associated with vehicle movement over time with respect to corresponding vehicle locations, dynamically adjust a predetermined speed limit setting based on the determined geo-location of the vehicle, detect whether an event has occurred based on the movement sensor output signals, the received unsafe driving parameters, the dynamically adjusted predetermined speed limit setting based on the determined geo-location of the vehicle, and the received driver's normal driving parameters, and generate a notification in response to detecting that the event occurred.

The device may include an identification unit that is configured to identify the driver and request the driver's normal driving patterns from the hosted server.

The identification unit may be further configured to identify the driver based on the driver's fingerprint, palm veins, face recognition, DNA, palm print, hand geometry, iris recognition, retina, scent, or any combination thereof.

The program instructions may be further configured to transmit the unsafe driving notification to the remote device via the communications device in accordance with the unsafe driving condition.

The program instructions may be further configured to transmit the unsafe driving notification to the hosted server via the communications device in accordance with the unsafe driving condition.

The device, the remote device, and the hosted server may be connected to each other via the communications network.

The unsafe driving notification generated in response to determining the unsafe driving condition may include a first type of unsafe driving notifications, wherein the program instructions are further effective upon execution by the processor to aggregate an amount of the first type of unsafe driving notifications generated during a particular driving session, compare the aggregated amount of the first type of unsafe driving notifications to a predetermined threshold value, and transmit the unsafe driving notification to the remote device via the communications device in accordance with the aggregated amount of the first type of unsafe driving notifications exceeding the predetermined threshold value.

The program instructions may be configured upon execution by the processor to determine the unsafe driving condition based on the movement sensor output signals, a predetermined speed limit setting associated with said vehicle location, and a predetermined absolute offset value with respect to the various speed limit settings.

The program instructions may be configured upon execution by the processor to determine the unsafe driving condition based on the movement sensor output signals, a predetermined speed limit setting associated with said vehicle location, and a predetermined percentage offset value with respect to the various speed limit settings.

The program instructions may be further configured upon execution by the processor to determine a change in movement by the vehicle from the movement sensor output signals, compare the determined change in movement by the vehicle to a rate of change threshold value, and determine an unsafe driving condition based on the determined change in movement by the vehicle exceeding the rate of change threshold value.

The housing may include a cigarette lighter plug or a 12 volt outlet configured to engage a cigarette lighter socket or a 12 volt outlet as said power source associated with the vehicle. The housing may further include an outlet that further includes less or more than 12 volts. The outlet may include a USB port.

The housing may further include: a first portion including the cigarette lighter plug or the 12 volt outlet configured on a first end for coupling to the cigarette lighter socket or the 12 volt outlet and positioned in a fixed manner relative to the vehicle when coupled thereto; a second portion coupled to the second end of the first portion and moveable between a first and a second position; and a locking mechanism effective to permit movement by the second portion relative to the first portion in a first state and to prevent movement by the second portion relative to the first portion in a second state.

The device may further include an audio sensor residing within the housing and functionally linked to the control unit, the program instructions further effective to receive audio output signals from the audio sensor and to determine a movement status associated with an accident based on the movement sensor output signals and the audio sensor output signals.

The device may further include an image sensor residing within the housing and effective to generate output signals associated with passengers in the vehicle The image sensor may be configured to determine passenger information in the vehicle based on the image sensor output signals and associated potential danger posed to the passengers, The passenger information may include weight, height, sex, age, and any other physical attributes of the passenger(s). The unsafe driving condition may be determined based on the passenger information. The vehicle may include at least one of: automobile, motorcycle, bike, submarine, boat, and/or airplane.

In yet another aspect of the present disclosure, one or more devices configured for coupling to respective vehicles and each including one or more sensors effective to generate output signals associated with positions and movements of the associated vehicle is disclosed. The device includes a hosted server network communicatively linked to each of the one or more devices via a communications network; a computer program product including one or more computer-readable memory media, the computer program product including program instructions executable by a processor to direct the performance of operations further including: receiving an array of data representative of predetermined speed limit settings for an associated array of geographical locations and a driver's normal driving parameters; storing said data in a database functionally linked to the memory medium and the processor; defining one or more unsafe driving locations in the array of geographical locations with respect to associated historical unsafe driving conditions and/or accidents and the driver's normal driving parameters; and for each of the respective vehicles to which one of the one or more devices are coupled, receiving position sensor output signals representative of vehicle position; receiving movement sensor output signals representative of vehicle movement; determining a location of the vehicle based on the position sensor output signals; determining a safe driving condition or unsafe driving condition based on the movement sensor output signals and at least a predetermined speed limit setting associated with said vehicle location; aggregating data associated with vehicle movement over time with respect to corresponding vehicle locations; dynamically adjusting the predetermined speed limit setting associated with one or more vehicle locations, based on the aggregated data; determining a potential unsafe driving condition based on the defined unsafe driving locations, the driver's normal driving parameters, the determined location of the vehicle, and the movement sensor output signals; and generating an unsafe driving notification in substantially real-time in response to determining an unsafe driving condition or a potential unsafe driving condition.

The program instructions may be executable to direct the performance of operations further including: transmitting an unsafe driving notification to a remote device via a communications device functionally linked to the processor and the memory medium in accordance with determined unsafe driving conditions.

The unsafe driving notification generated in response to determining an unsafe driving condition may include a first type of unsafe driving notification, wherein the program instructions executable by the processor to direct the performance of operations further including: aggregating an amount of the first type of unsafe driving notification generated during a particular driving session, comparing the aggregated amount of the first type of unsafe driving notification to a predetermined threshold value, and transmitting an unsafe driving notification to the remote device in accordance with the aggregated amount of the first type of unsafe driving notifications exceeding the predetermined threshold value.

The program instructions executable by the processor to direct the performance of operations further may include determining the safe driving condition or the an unsafe driving condition based on the movement sensor output signals, a predetermined speed limit setting associated with said vehicle location, and a predetermined absolute offset value with respect to the various speed limit settings.

The program instructions executable by the processor to direct the performance of operations further may include determining the safe driving condition or the unsafe driving condition based on the movement sensor output signals, a predetermined speed limit setting associated with said vehicle location, and a predetermined percentage offset value with respect to the various speed limit settings.

The program instructions executable by the processor to direct the performance of operations may further include: determining a change in movement by the vehicle from the movement sensor output signals, comparing the determined change in movement by the vehicle to a rate of change threshold value, and determining the unsafe driving condition based on the determined change in movement by the vehicle exceeding the rate of change threshold value.

The operation of dynamically adjusting the speed limit setting may include disregarding vehicle movement data for respective vehicle locations outside of a threshold deviation value, and adjusting the speed limit settings based on one or more of a determined average speed and a determined median speed from the remaining vehicle movement data.

The at least one of the one or more devices may include a cigarette lighter plug or 12 volte outlet configured to engage a cigarette lighter socket as a power source associated with a respective vehicle, the at least one device positioned in a fixed manner relative to the respective vehicle when coupled thereto.

The at least one of the one or more devices may further include: a first portion including the cigarette lighter plug configured on a first end for coupling to the cigarette lighter socket and positioned in a fixed manner relative to the respective vehicle when coupled thereto; a second portion coupled to the second end of the first portion and moveable between a first and a second position; and a locking mechanism effective to permit movement by the second portion relative to the first portion in a first state and to prevent movement by the second portion relative to the first portion in a second state.

The at least one of the one or more devices may further include an audio sensor, the program instructions further executable to receive audio output signals from the audio sensor and to determine a movement status associated with an accident based on the movement sensor output signals, the audio sensor output signals and one or more accident threshold settings.

An aspect of the present disclosure provides a computer readable storage medium tangibly embodying a computer readable program code having computer readable instructions which, when implemented, cause a computer to carry out the steps of a method as described herein.

In yet another aspect of the present disclosure, a system for detecting an occurrence of an event in a vehicle is provided. The system includes a device positioned in the vehicle and configured to measure data and to detect whether an event has occurred based on the measured data, responsive to the device detecting that the event has occurred, the device is configured to transmit an output signal associated with the event; a remote device configured to receive the output signal from the device and to display, on a display device of the remote device, a message associated with the detected event; and a computing device configured to receive the output signal from the device and to display, on a display device of the computing device, the message associated with the detected event, the computing device including a user interface for permitting an emergency response professional to customize options associated with monitoring messages associated with a plurality of detected events, wherein the device, the remote device, and the computing device are communicatively connected via a communications network. The event may be an accident involving the vehicle or an unsafe driving condition of the vehicle.

The message associated with the detected event may be displayed on the display device of the computing device in real-time.

In yet another aspect of the present disclosure, a system for detecting an occurrence of an event in a vehicle is provided. The system includes a device positioned in the vehicle and configured to collect and transmit a data set; a remote device configured to receive the data set from the device and to display, on a display device of the remote device, a message associated with the data set; a computing device configured to receive the data set from the device and to display, on a display device of the computing device, the message associated with the data set, the computing device including a user interface for permitting an emergency response professional to customize options associated with monitoring messages associated with a plurality of data sets; and a server storing data associated with a base driving pattern of a driver of the vehicle, the server configured to receive the data set from the device, the data set including data associated with a current driving pattern of the driver of the vehicle, wherein the device, the remote device, the computing device, and the server are communicatively connected via a communications network.

The server may be configured to compare the data associated with the current driving pattern of the driver of the vehicle with the data associated with the base driving pattern of the driver of the vehicle to detect whether an event has occurred.

The event may be an unsafe driving condition of the vehicle or a potentially unsafe driving condition of the vehicle.

The server may be configured to send a notification to the remote device, the computing device, or both, responsive to the server detecting that the event has occurred.

Another aspect of the present disclosure provides a housing configured to be coupled to a power source of a vehicle, the housing being fixed relative to the vehicle when coupled thereto; a power supply in the housing and configured to receive power from the power source of the vehicle when the housing is coupled thereto; a movement sensor in the housing and configured to generate output signals associated with movement of the vehicle; a geo-location sensor in the housing and configured to generate output signals associated with a geo-location of the vehicle; a communications module in the housing and configured to send and receive data via a communications network; and one or more controllers configured to: receive base driving parameters for a driver via the communications device, receive unsafe driving parameters via the communications device, determine a geo-location of the vehicle based on the geo-location sensor output signals, dynamically adjust a predetermined speed limit setting based on the determined geo-location of the vehicle, detect whether an event has occurred based on one or more of (i) the output signals of the movement sensor, (ii) the received unsafe driving parameters, (iii) the dynamically adjusted predetermined speed limit setting, and (iv) the received base driving parameters for the driver, and in response to detecting that the event occurred, generate a notification associated with the detected event.

BRIEF DESCRIPTION OF THE SEVERAL VIEWS OF THE DRAWINGS

FIG. 5 is a block diagram representing an implementation of a device configuration according to the present disclosure.

FIG. 6 is a block diagram representing another implementation of a device configuration according to the present disclosure.

FIG. 7 is a block diagram representing another implementation of a device configuration according to the present disclosure.

DETAILED DESCRIPTION OF THE DISCLOSURE

Figure 1:
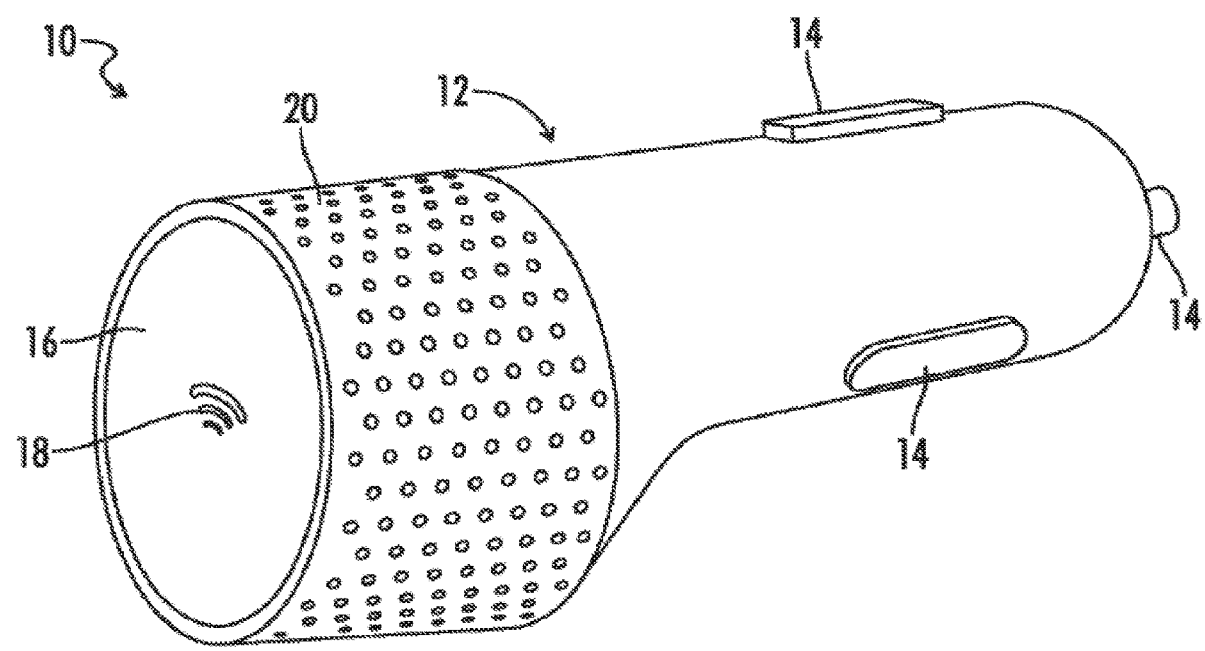
FIG. 1 is a front isometric view of a device according to an implementation implementation of the present disclosure.

The disclosure and the various features and advantageous details thereof are explained more fully with reference to the non-limiting implementations and examples that are described and/or illustrated in the accompanying drawings, the "ATTACHMENT", and detailed in the following description. It should be noted that the features illustrated in the drawings and the ATTACHMENT are not necessarily drawn to scale, and features of one implementation may be employed with other implementations as any person skilled in the art would recognize, even if not explicitly stated herein. Descriptions of well-known components and processing techniques may be omitted so as to not unnecessarily obscure the implementations of the disclosure. The examples used herein are intended merely to facilitate an understanding of ways in which the disclosure may be practiced and to further enable those of skill in the art to practice the implementations of the disclosure. Accordingly, the examples and implementations herein should not be construed as limiting the scope of the disclosure.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one implementation," as used herein does not necessarily refer to the same implementation The term "coupled" means at least either a direct electrical connection between the connected items or an indirect connection through one or more passive or active intermediary devices. The term "circuit" means at least either a single component or a multiplicity of components, either active and/or passive, that are coupled together to provide a desired function. The term "signal" as used herein may include any meanings as may be understood by those of ordinary skill in the art, including at least an electric or magnetic representation of current, voltage, charge, temperature, data or a state of one or more memory locations as expressed on one or more transmission mediums, and generally capable of being transmitted, received, stored, compared, combined or otherwise manipulated in any equivalent manner.

Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, a cloud, a super computer, a personal computer, a laptop computer, a palm-top computer, a mobile device, a tablet computer, a notebook computer, a desktop computer, a workstation computer, a server, or the like, or an array of processors, microprocessors, central processing units, general purpose computers, super computers, personal computers, laptop computers, palmtop computers, mobile devices, tablet computers, notebook computers, desktop computers, workstation computers, servers, or the like.

A "server," as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

A "database," as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communications network," as used in this disclosure, means a wired and/or wireless medium that conveys data or information between at least two points. The wired or wireless medium may include, for example, a metallic conductor link, a radio frequency (RF) communication link, an Infrared (IR) communication link, telecommunications networks, an optical communication link, internet (wireless and wired) or the like, without limitation. The RF communication link may include, for example, WiFi, WiMAX, IEEE 802.11, DECT, 0G, 1G, 2G, 3G, 4G, 5G or future cellular standards, Bluetooth, Bluetooth Low Energy, NFC, ultrasound, induction, laser (or similar optical transmission) and the like.

A "computer-readable storage medium," as used in this disclosure, means any medium that participates in providing data (for example, instructions) which may be read by a computer. Such a medium may take many forms, including non-volatile media, volatile media, and transmission media. Non-volatile media may include, for example, optical or magnetic disks, flash memory, and other persistent memory. Volatile media may include dynamic random access memory (DRAM). Transmission media may include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, or the like.

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, the cloud network, or the like, or any combination of the foregoing, any of which may be configured to communicate data via a wireless and/or a wired communication medium. These networks may run a variety of protocols not limited to TCP/IP, IRC, SSL, TLS, UDP, or HTTP.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

Referring generally to FIGS. 1-13, various implementations of systems, devices, and methods in accordance with the present disclosure may be described herein. Where the various figures may describe implementations sharing various common elements and features with other implementations, similar elements and features are given the same reference numerals and redundant description thereof may be omitted below.

Generally stated, a local device is configured in accordance with the present disclosure to detect a vehicle status, such as for example an accident or even unsafe driving conditions, and provide output signals to local and/or remote devices or indicators representative of vehicle data and vehicle status. A host system may include a central server configured to send and receive data to and from the device, and a user interface such as for example a hosted web site generated via the central server or a program application downloaded to and generated from a remote user device such as for example a smartphone, the user interface being optionally configured to display the vehicle data and status received from the local device and/or to receive remote user input for programming the local device. The local device may in various implementations be a dedicated or stand-alone device for use in (and powered by a power source associated with) a vehicle such as for example a cigarette lighter adapter as further described below, or may be a computing device having numerous alternative uses such as for example a smartphone running a dedicated program application.

Figure 2:
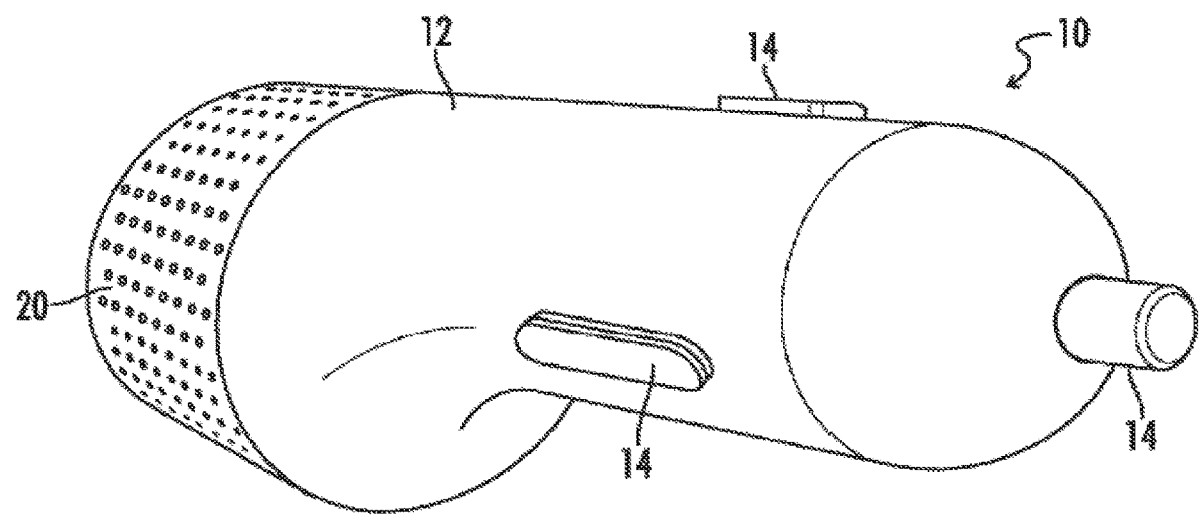
FIG. 2 is a rear isometric view of the device of FIG. 1.

Referring first to FIGS. 1-2, front and rear isometric views are shown representing an implementation of a standalone local device 10 in accordance with the present disclosure. An integral housing 12 is shown here which includes power supply terminals 14 on a first end defining a cigarette lighter plug for coupling to an onboard power supply of a vehicle such as a cigarette lighter socket, although in various implementations (not shown) the local device 10 may include alternative power supply terminals or power input means to receive power from an alternative local power source.

As the local device protrudes outward from the cigarette lighter socket of a vehicle when it is plugged in, in other implementations (not shown) it may be desirable that the housing 12 include a bendable, rotatable or otherwise moveable portion which may allow an opposing or distal end of the housing 12 with respect to the cigarette lighter plug leads 14 to be positioned in a practical fashion and thereby accommodate varying vehicle interior designs. In such implementations, the moveable portion of the housing 12 may further include a locking mechanism such as a latch that prevents the moveable portion from moving relative to the first end (i.e., the cigarette lighter plug) once it is locked into position.

Figure 3:
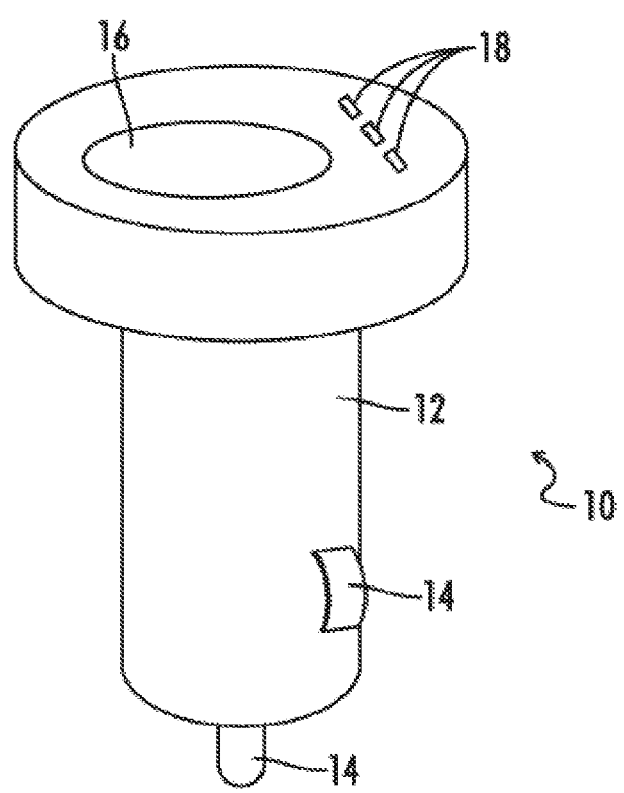
FIG. 3 is a front isometric view of a device according to another implementation of the present disclosure.

The distal end of the device 10 as shown in FIGS. 1-2 further includes a button 16 as a local user interface occupying some portion of a face (or otherwise disposed along a length of the housing 12) which may be used for engaging the device 10 and causing internal control circuitry to perform predetermined functions as further described below. The distal end may further include other visual indicators 18 such as for example a plurality of LED outputs 18 located within the button 16 (as shown in FIG. 1) or on a portion of a face of the distal end proximate the button 16 (as shown in FIG. 3), or any other practical and visually accessible location about the housing 12. The various visual indicators 18 may be configured to indicate to a driver that the device is functional, or may be an indicator of driving performance or some other predetermined indicator as programmed into the device 10. In a particular exemplary implementation, the device 10 may include three lights arranged to be visible to a driver when plugged into the cigarette lighter socket and colored green, yellow and red to indicate driving performance.

Another portion of the housing 12 may include slits, holes or by other or other equivalent openings 20 to allow for audio input and output with respect to internal components such as a microphone, etc. In various implementations (not shown) the device 10 may contain a connector and/or cable for the purpose of physically connecting to another device, such as a 30-pin cable which may or may not be detachable from the device 10. The device 10 may further contain a small pin-sized button (not shown) that is not easily depressed for the purposes of programming the device 10.

Figure 4:
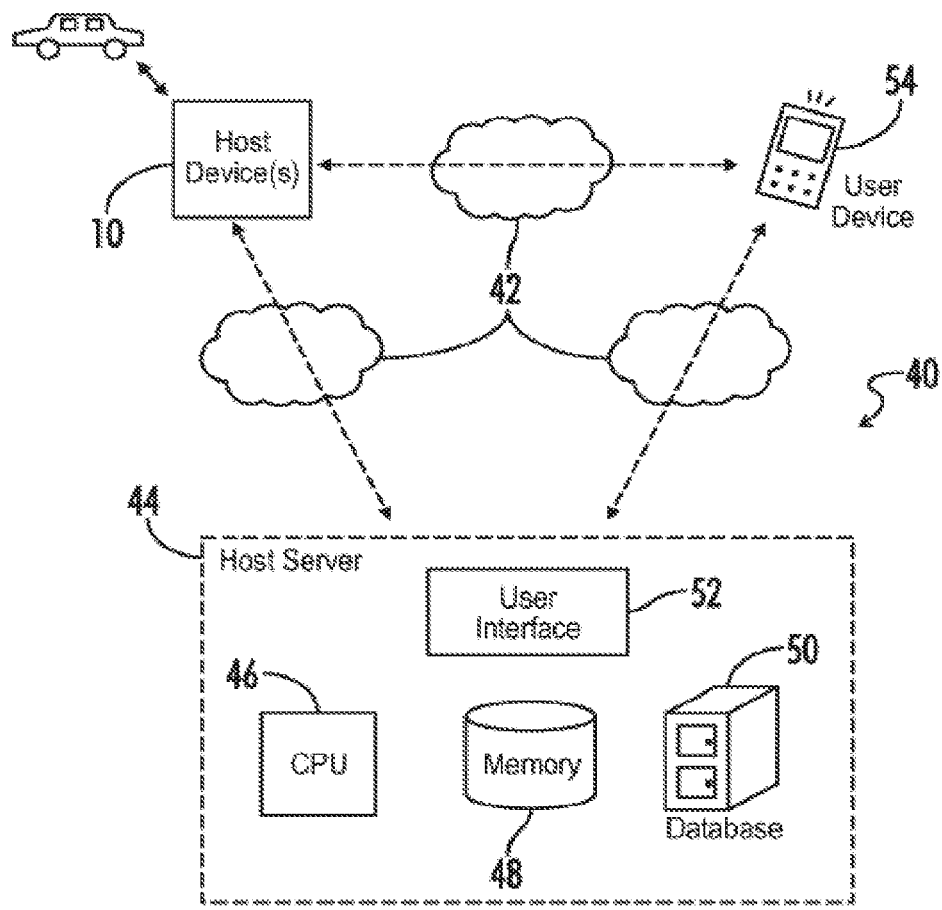
FIG. 4 is a block diagram representing a host system according to an implementation of the present disclosure.

Referring now to FIG. 4, an exemplary hosted system 40 according to an implementation of the present disclosure may include a server 44 functionally and communicatively linked to the local device 10 via a communications network 42. Alternatively, a distributed server network may be used to provide or facilitate the same functions.

The hosted server 44 in the example shown may include without limitation one or more processors 46, a computer-readable memory medium 48 and a database 50. The term "computer-readable memory medium" as used herein may refer to any non-transitory medium alone or as one of a plurality of non-transitory memory media within which is embodied a computer program product that includes processor-executable software, instructions or program modules which upon execution may provide data or otherwise cause the server 44 or equivalent computer system to implement subject matter or otherwise operate in a specific manner as further defined herein. It may further be understood that more than one type of memory media may be used in combination to conduct processor-executable software, instructions or program modules from a first memory medium upon which the software, instructions or program modules initially reside to a processor for execution.

"Memory media" may further include without limitation transmission media and/or storage media. "Storage media" may refer in an equivalent manner to volatile and non-volatile, removable and non-removable media, including at least dynamic memory, application specific integrated circuits (ASIC), chip memory devices, optical or magnetic disk memory devices, flash memory devices, or any other medium which may be used to stored data in a processor-accessible manner, and may unless otherwise stated either reside on a single computing platform or be distributed across a plurality of such platforms. "Transmission media" may include any tangible media effective to permit processor-executable software, instructions or program modules residing on the media to be read and executed by a processor, including without limitation wire, cable, fiber-optic and wireless media such as is known in the art.

The software products residing on the hosted server 44 may be effective to for example generate a user interface 52 such as a website and associated web pages to display data received from the local device 10 or receive data from a user for programming the local device 10. Data from the local device 10 may further be stored in the database 50 in an account associated with a user and used for data trending or other intermediate- to long-term statistical analysis or reporting. The hosted server 44 may further provide software products for downloading via the user interface 52 or by other known transmission media (or via third party servers such as for example conventionally known mobile application markets) to a user device 54 such that upon execution of a host-provided program the user may be able to remotely access data from the local device 10 or otherwise program the local device 10 via a communications network 42 without further requiring the use of the host system 40 as an intermediary. The remote user device 54 may include any of a number of computing devices including desktops, laptops, tablets, smart-phones, etc., as operable to download the software products and execute the associated program features as described above. The user device 54 as represented in FIG. 4 may in various implementations cover more than just a device associated with a user wishing to view data associated with the vehicle, but also may cover devices for predetermined contacts or emergency medical service personnel that may be programmed with respect to the local device 10 as automatic contacts in the event of an emergency.

Figure 8:
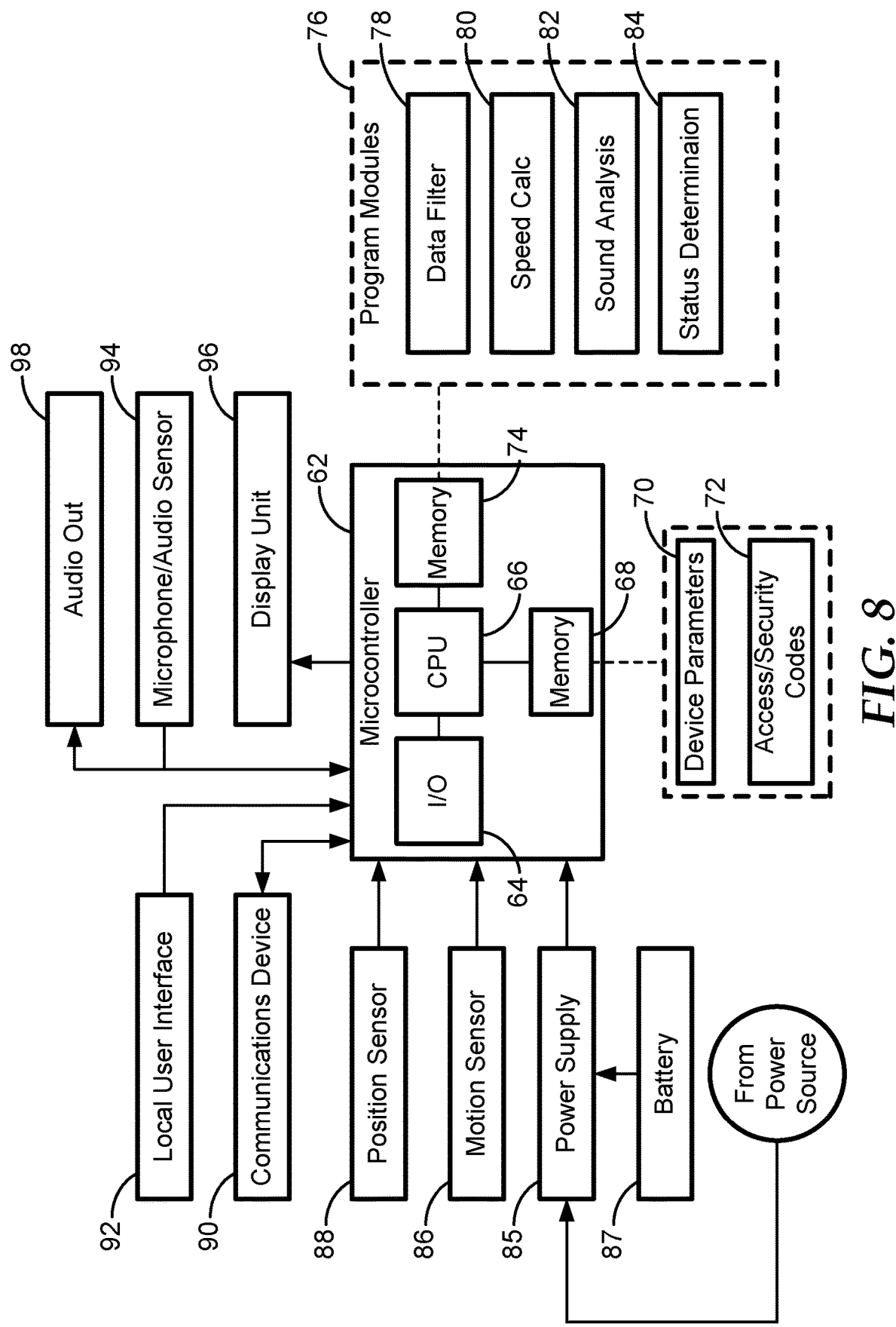
FIG. 8 is a block diagram representing internal components of an exemplary device according to an implementation of the present disclosure.

Referring now to FIG. 8, the various internal components of an exemplary device 10 in accordance with an implementation of the present disclosure may include a control unit 62 such as a conventional microcontroller having an I/O module 64, a processing unit 66, a memory 68 effective to store for example device parameters 70 and relevant access or security codes 72 and a memory 74 upon which resides instructions or program modules 76 such as for example a data filtering module 78, a speed calculation module 80, a sound analysis module 82 and a vehicle status determination module 84.

While the terms "controller" or "control unit" as used interchangeably herein may typically refer to a microcontroller designed as described above and further programmed to perform functions as further defined herein, it may in various alternative implementations refer to for example a general microprocessor, an application specific integrated circuit (ASIC), a digital signal processor (DSP), a field programmable gate array, and/or various alternative blocks of discrete circuitry as are known in the art to perform functions as defined herein when so configured.

It may further be understood that the internal components of the control unit are not limited to those described herein, that some of the circuitry or program modules described herein may in fact be redundant or unnecessary for a particular application, and that in various implementations two or more of the program modules described may in fact describe a single program module effective to perform like functions.

Further residing within or about the device housing(s) 12 and functionally linked to the controller 62 may be without limitation a vehicle motion sensor 86 such as an accelerometer and/or gyroscope, a position sensor 88 such as a conventional GPS receiver, a communications device 90 such as a cellular modem, a local user interface 92 such as for example the button described above, a microphone 94 or equivalent audio sensor, a display unit 96 such as for example the LEDs or other visual outputs, and an audio output 98 effective to for example beep, ring or otherwise alert the driver based on a programmed function. As but one further example, the audio output 98 may be effective to provide real-time voice functionality in addition to programmed alerts, such as may be desirable in the event of an emergency by providing emergency personnel, 911 operators, etc., with a direct outlet for communicating via the local device with a driver. The real-time may mean same time or substantially same time (e.g., within milliseconds). The real-time may mean greater or less than 1 millisecond.

Even further residing within the device housing 12 as represented in FIG. 8 are an internal power supply 85 which may be coupled to the external (onboard) power source 56 via for example the various contact terminals 14, and an energy storage device 87 such as for example a battery or a capacitor. In various implementations, the controller may be effective to determine whether the removal of input power from the power source (via the contact terminals) is a result of being forcibly ejected from the power source such as may be the case in an accident, or merely having been removed manually by the user. In the event that the device 10 is determined to have been forcibly ejected (removed from the power source), the power supply 85 may be triggered to switch from the power source 85 as a primary power input source to the energy storage device 87 as a secondary source, which may be configured to store at least enough power that the microcontroller will have a period of time to generate and transmit an event alert such as a voice call to a remote entity (i.e., 911). The device 10 may preferably include program instructions effective to execute a process for determining forcible ejection, which may in certain implementations include confirming an accident condition in a manner substantially as recited below and coincident with detection of the lack of power from the primary source 56. In alternative implementations the process for determining forcible ejection may be substantially independent from or otherwise unrelated to the processes described herein for determining an accident condition.

It may be understood by those of skill in the art that one or more of the components described above as residing within the housing may be combined into a single component having the equivalent features. For example, a communications device could within the scope of the present disclosure further potentially serve as the positioning sensor. It may further be understood that one or more of the above-described components may in fact be unnecessary or redundant for a particular application still within the scope of the present disclosure, and the list of components is in no way intended as limiting.

Referring now to FIGS. 5-7, various implementations of a local device configuration may be briefly described.

In one implementation as represented in FIG. 5, a local device 10 is fixed in position when plugged into the onboard power source 56 and effective to transmit and receive data to and from a remote device (i.e., smartphone, desktop, tablet, etc.) and/or the host server 44 via a communications network as substantially described above.

In another implementation as represented in FIG. 6 (i.e., the so-called "pregnant snake" configuration) the device 10 is divided up into a first device module 58 which is coupled to the onboard power source 56 and a second device module 60 which is able to communicate with the remote devices 54 and/or the hosted server 44 via the communications network 42. Several of the internal components such as for example the GPS receiver, cellular modem, microcontroller and accelerometer may reside in the second module 60 and be electrically coupled to the first module 58 and the associated power supply via a cord. The first module 58 may still have a front face upon which the button is supported, but in this configuration the first module 58 or otherwise the portion of the device 10 which is physically coupled to the cigarette lighter socket may be smaller as needed or otherwise desirable. The second module 60 in this implementation would still need to be rigidly attached to the vehicle interior by a bracket or equivalent attachment mechanism in order for the accelerometer to function reliably. To escape the need to securely stabilize the components not contained in the first module 58, however, the accelerometer could alternatively be placed into the first module 58 and thereby fixed in position relative to the vehicle while the remaining components are not fixed but remain electrically coupled to the power supply via a wire.

In another implementation as represented in FIG. 7, the local device 10 may embody two separate devices 10*a*, 10*b* respectively coupled to two separate onboard power sources 56*a*, 56*b* around the vehicle. Either or both of the separate devices may be further separated into a first module 58*a*, 58*b* and a second module 60*a*, 60*b* as described with respect to the implementation shown in FIG. 6. Through RF technology or an equivalent these otherwise independent devices may communicate with each other and function as a single device or local system having redundancy features such as for example confirmation of a detected vehicle status.

As previously described or otherwise implied above, a local device 10 in accordance with various implementations of the present disclosure may communicate and interact with other devices via a connector and/or cable such as for example a 30-pin cable or an embedded communications device such as an RF module. The device can communicate with a mobile cellular device, another device connected to an onboard vehicle data gathering module (e.g., via an OBD-II port as is known in the art), other sensor devices attached to the vehicle, and/or devices used to communicate with the driver in the vehicle. Interaction between a mobile cellular device and the local device 10 may be for the purpose of programming or setting up the local device 10 and/or viewing data from the local device 10. Interaction between a device connected to the OBD-II port and the local device 10 may further be established for the purpose of collecting data from the vehicle which would otherwise be unavailable but useful within the scope of the present disclosure, or even for the purpose of allowing the local device 10 to operate alternative vehicle functions such as for example the opening or locking of car doors, windows, trunk, etc. This data may include without limitation vehicle speed, airbag deployment, vehicle braking, and various additional information as may be supplied from the engine control unit (ECU).

Also as previously mentioned, the local device 10 may have a small button associated with the housing for user programming. Alternatively or in addition, it may be desirable to provide another physical input/output port on the device housing such as for example a USB port for external cable connection and programming, or even a USB cable connector integral with or otherwise for example extendable from the housing to establish a connection with a USB port of a programming device. However, in various implementations it may be desirable to omit such a physical programming mechanism and instead rely on wireless programming methods. One such method for programming the local device 10 may include accessing the hosted user interface (website) where some or all of the device/system parameters may be setup and then a message sent to the local device 10 to adjust the settings. This may generally involve providing a list of programmable settings for user selection, and subsequently providing either a data entry field or a series of user selectable parameters in association with each selected program setting. The predetermined contact information (e.g., telephone numbers) to be used by the local device in case of an accident or other predetermined extreme event via text messaging (e.g., SMS) can also be programmed through the website. The local device may further include an identification code and/or security code which is further entered via the website so that for example the website knows which device to program or confirms that authorization exists for the same.

In addition, or in the alternative, programming for the local device may be carried out via a mobile computing device such as for example a smartphone, for example wirelessly or using a hardware connector that is attached to the device. Setup proceeds in substantially the same manner or via similar pathway as that described with respect to the website. As an alternative to entering a device-specific code, there may in certain implementations be a predetermined radius of for example several feet around the local device where a remote device can auto-connect with the local device and allow programming through the local device's RF module (or equivalent). This auto-connect feature may be for example triggered by the depressing of a small-pin sized programming button on the device.

In various implementations, the local device may be programmed to continuously collect and transmit data associated with the vehicle to the host server for storage in the database. Further, the local device processes vehicle data to determine vehicle status conditions such as for example an emergency event/accident, or more broadly a driving status which may include safe, unsafe or merely cautionary status modes. In other implementations within the scope of the present disclosure, the vehicle status conditions may be determined remotely on for example the host server based on received data associated with the vehicle having been transmitted on a more or less continuous basis via the communications network.

Figure 9:
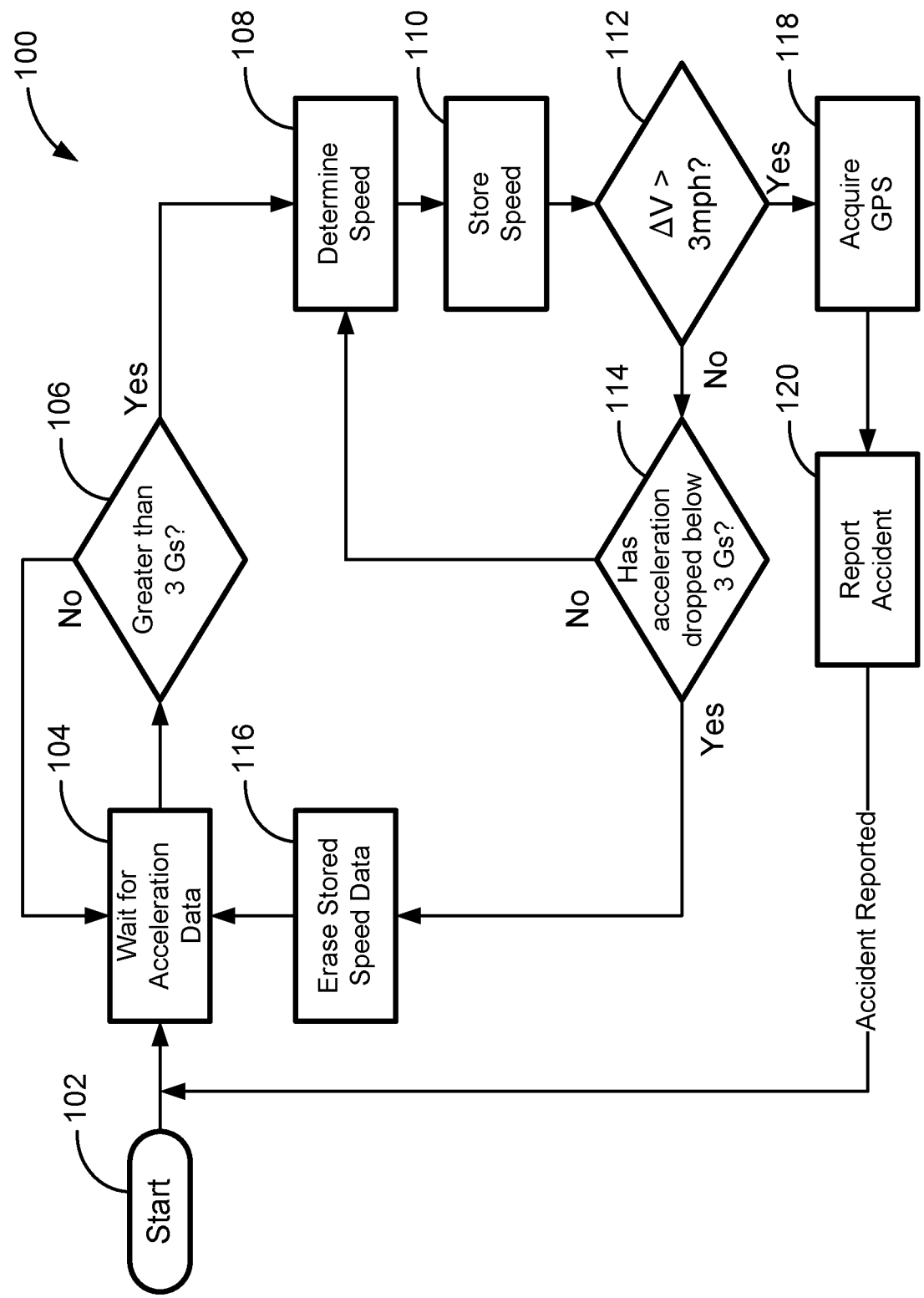
FIG. 9 is a flowchart representing an implementation of an exemplary method for detecting a vehicle status, more particularly an accident, in accordance with the present disclosure.

Referring now to FIG. 9, an exemplary implementation of a method 100 for determining an accident condition as a vehicle status may be described. The method 100 may be executed in accordance with a computer program product as described above, and the platform for executing data communications and program functions included herein may include without limitation an interrupt-driven, event-driven, and/or polling architecture as well as any equivalents as are conventionally known in the art.

The process may start (at step 102) upon power being initially provided to the local device via vehicle ignition, initial plug-in to the onboard power source, etc. Once power has been supplied to the device, the microcontroller waits for acceleration data to be received from the accelerometer of the local device (step 104). If the acceleration data is greater than a predetermined acceleration threshold of for example 3G's (i.e., "no" in response to the query of step 106), the process returns to step 104 and continues to monitor the acceleration data. If an acceleration reading (or alternatively a set of acceleration readings where the data may be averaged and filtered for any of various reasons) exceeds the acceleration threshold (i.e., "yes" in response to the query of step 106), the process continues to step 108 and the vehicle speed may be determined. In certain implementations the device may rather than relying on a predetermined acceleration threshold include neural network processing algorithms for recognizing vehicle acceleration patterns and comparing current vehicle acceleration data with an acceleration threshold that has been determined by the microcontroller, perhaps as adjusted from a predetermined initial acceleration threshold in view of the recognized patterns.

Upon determining a vehicle speed or a series of two or more vehicle speed readings (step 108) and storing the vehicle speed reading(s) (step 110), the process then determines whether the change in speed is consistent with an accident in view of for example a change in speed being greater than a second predetermined threshold (step 112). If the change in velocity is less than the second predetermined threshold (or for example where only one velocity reading has been taken and therefore no rate of change can be determined) the process is then directed to step 114. If a subsequent acceleration reading determines that the vehicle acceleration has dropped below the first threshold (i.e., "yes" in response to the query in step 114), the process continues by erasing the stored velocity data (step 116) and then returns to step 104. If the vehicle acceleration remains above the first threshold (i.e., "no" in response to the query in step 114) the process returns to step 108 and the microcontroller takes additional velocity readings.

If at any point a vehicle acceleration reading is determined to be greater than the first threshold and the change in vehicle velocity is determined to be greater than the second threshold (i.e., "yes" in response to the query in step 112) the process continues by acquiring position coordinates for the vehicle via the position sensor/GPS (in step 118) and then reporting the accident pursuant to programmed instruction by for example transmitting vehicle position data and other programmed data to predetermined personnel such as EMS, family, friends, etc. (in step 120). In this manner detailed feedback regarding specifics of an accident may be provided, such as for example how the accident occurred, the order and direction of impacts over the course of the accident. This information may be used to estimate likely injuries to passengers in the vehicle and assist emergency personnel in allocating resources for dispatch to the emergency site.

Various additional modes of operation as further described below but without limitation to the specific modes recited herein may be activated by the user via engaging of the main button on the device housing. The local device may be programmed to perform any one or more of the modes upon activation or engaging of the button based for example on user selections via either or both of the host website or a program application via a remote computing device (i.e., smartphone handset).

In one exemplary mode of operation, the local device may have been programmed to treat the button as a help button, wherein upon activation of the button by a user the local device transmits an SMS and/or email message to a predetermined number and/or address with for example an alert and the location of the vehicle as determined from the GPS receiver. In an implementation, activation of the button may automatically trigger a call to a public safety answering point (i.e., 911), which may be supplemental rather than merely an alternative to other predetermined contacts and/or addresses. The voice call may in fact be preferable over the SMS option as a mistaken activation of the button may be easily identified by the emergency personnel.

In another exemplary mode of operation, the local device may have been programmed to treat the button as a position indication and notification button, wherein upon activation of the button by a user the local device transmits a vehicle location as determined from the GPS receiver to a predetermined location such as for example a social networking site associated with the driver, a group, a destination, etc. In this manner a user that is running late for an event may notify others collectively without sending several individual text messages or email messages.

In another exemplary mode of operation, the local device may have been programmed to treat the button as a tracking toggle button, wherein upon engagement of the button by a user a tracking feature is successively activated and deactivated. The tracking feature may include continuous transmission of vehicle position data and any other appropriate data as received or determined by the local device to a remote site such as the host website. One example of a tracking feature may include the tracking of service personnel, where the local device is plugged into a service provider's vehicle and customers of the service provider who are waiting for service can use the host website (or alternatively a web portal associated with the service providers themselves where such features are appropriately established) to actively track the current status of the vehicle along a service route (for example) and better determine when they can expect service. In a second example, the local device may be plugged into a delivery vehicle (i.e., mail, FedEx) to facilitate the tracking of packages that have been confirmed as loaded onto the particular vehicle. The present status of the button (i.e., the underlying tracking feature) may be indicated to the user by for example a light or through the use of an audio signal via the speaker.

In another exemplary mode of operation, the local device may have been programmed to treat the button as a business mileage logging button, wherein upon engagement of the button by a user a business mileage logging feature is successively activated and deactivated. When the feature is activated, the local device may be programmed to send a message to a remote program that keeps track of business mileage. The message may include a current odometer reading, wherein the remote program can perform business mileage calculations based on a previous message and associated odometer reading. Alternatively, the local device may be programmed to begin tracking mileage upon a first engagement of the button, and upon a second engagement of the button to determine a mileage since the first engagement and to transmit a message including the determined mileage to a remote program.

In another exemplary mode of operation, the local device may be programmed to treat the button as an "I'm Lost" button, wherein upon engagement of the button by a user the local device transmits an email to a predetermined contact along with the vehicle location on a map and a request to call the user.

In another exemplary mode of operation, the local device may be programmed upon engagement of the button by a user to record a sound clip or sound message and subsequently to transmit the recorded sound clip or message to a predetermined destination such as for example one or more email addresses or a social networking site (i.e., Facebook, Twitter, etc.). The sound clip or message may be recorded for a pre-determined length of time after the button has been initially engaged, or alternatively the local device may be programmed to record a sound clip or message for as long as the button remains engaged by the user, either by remaining depressed or, as with the tracking feature, by remaining in a toggled "on" or "off" position.

In another exemplary mode of operation, the local device may be programmed upon engagement of the button by a user to transmit a message including vehicle location data received via the GPS receiver to a predetermined website. The website may be configured to generate and place a pin or equivalent indicator on an associated map upon receiving the message, wherein the user may later access the map and see and label the "pins" on the map without forgetting their location. The website may further associate other data such as for example a time stamp, a user identifier, voice clip taken from the device, etc., with the location "pin".

Figure 10:
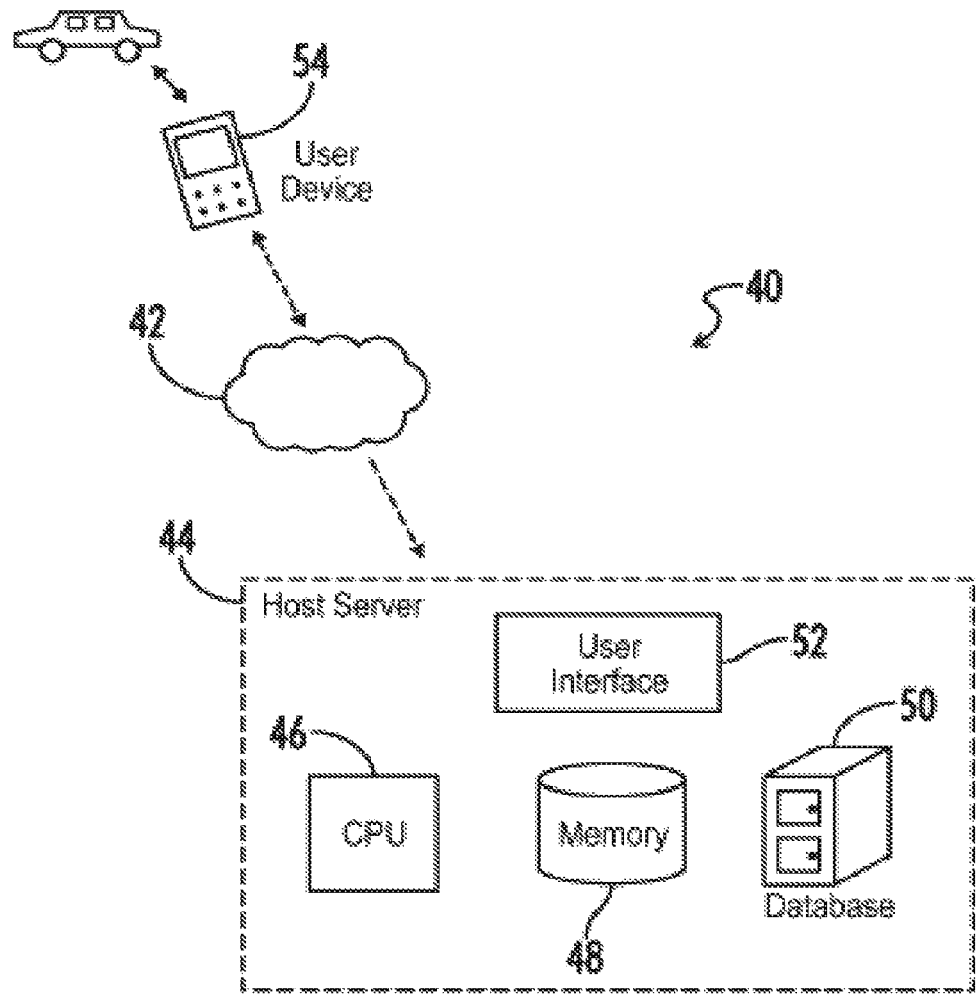
FIG. 10 is a block diagram representing a host system according to another implementation of the present disclosure.

Referring now to FIG. 10, in an implementation the local device 10 as a cigarette lighter adapter may be replaced by a computer program product installed on and executable by a mobile cellular device 54 such as for example a smartphone. The mobile cellular device 54 may be any of a number of equivalent devices (such as for example the iPhone by Apple) as are equipped with onboard sensors that in combination with the computer program product are effective to provide automatic crash notification and event data recording within the scope of the present disclosure. Such onboard sensors (not further shown in the various figures) include but are not limited to the accelerometer/gyroscope, GPS receiver and microphone.

The computer program product may upon execution by the device 54 generate a user interface on the associated display screen by which the various parameters for the program may be set by the user, as well as display collected vehicle data, vehicle status information and other visual indications or cues as programmed. An example of such a visual indication may be a current speed limit for a particular stretch of road which is recognized by the program based on a GPS-determined location and comparison of the location with that same location on a digital map having speed limit data, as may be further described below.

Figure 11:
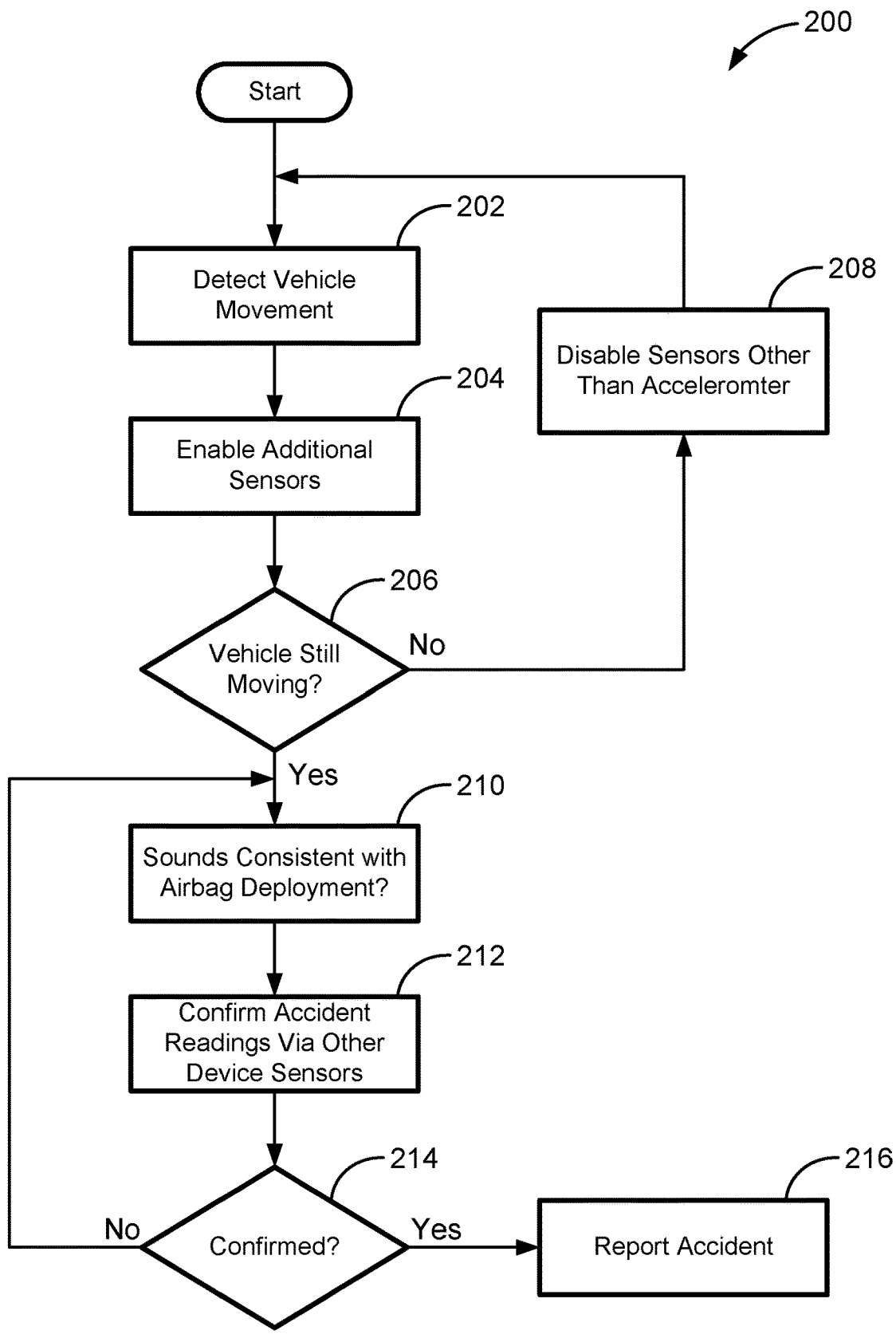
FIG. 11 is a flowchart representing an implementation of another exemplary method for detecting a vehicle status, more particularly an accident, in accordance with the present disclosure.

Referring to FIG. 11, another method 200 of detecting a vehicle status and more particularly an accident condition, as may be performed by a computer program product executed from a smartphone, may include supplementing of movement data as described above by further using sound data.

The previously described method 100 determined an accident based upon acceleration and rate of change in velocity readings that are consistent with an accident, and consequently with conditions under which airbag deployment would be expected in theory but without explicit confirmation. In an effort to eliminate false positives, the data from the accelerometer/gyroscope may be substantiated using the microphone to detect the impulse/noise physically generated by airbag deployment or an equivalent sound sufficiently representative of an accident. As embodied in the algorithms of the computer program product of the present disclosure, this allows for the mobile cellular device 54 to detect and explicitly confirm accidents where for example the airbag is in fact deployed, or at least is determined to have been employed with a substantially higher degree of certainty.

The process may begin in step 202 by confirming that the mobile device is in fact located in a moving vehicle. Since a mobile cellular device does not remain in a vehicle at all times, such an assessment is necessary to avoid false positives. This can be done by using the GPS receiver, accelerometer or various combinations of sensors to discern when conditions being experienced by the device are consistent with being in a vehicle. The real time detection of circumstances allows the application to run in the background of the mobile cellular device 54 without the program being executed to assess movements for potential crashes when otherwise not applicable. In an alternative implementation, however, this step may be omitted or skipped by programming the device to perform the vehicle status determination sequence only upon manual execution of the program by a user rather than automatically detecting vehicle movement.

In an effort to conserve battery life, in various implementations the accelerometer may be the only sensor that runs the entire time that the program product is engaged. Typically, when the program is passively running in the background it only draws data constantly from the accelerometer. The data from the accelerometer is used to determine when the device 54 (handset) is transported into the interior of a moving vehicle. This change in environment can be discovered using velocity and duration of velocity data, as the speed achieved in a moving vehicle coupled with the time spent at that speed is only rarely achieved outside of a moving vehicle. Velocity data can be garnered by integrating the acceleration data from the accelerometer as the area under the acceleration curve is the velocity.

However, while the accelerometer can detect changes in velocity it cannot detect absolute velocity without being made aware of initial velocity (a reflection of the unknown variable that results when integrating). This means that after the program is launched initial velocity will first need to be calculated by enabling the additional sensors (step 204) and then using the GPS receiver. Ideally, absolute velocity would only need to be calculated once when the program is initiated and after that point would be accurately updated using the accelerometer data. Due to accuracy issues, however, using the accelerometer data alone is not sufficient to maintain accurate absolute velocity. In order to maintain a precise velocity value over time, the initial velocity may be updated via the GPS receiver. This update process may happen based on a set value that determines how often this occurs, such as for example every ten minutes. Assuming that the accelerometer data indicates the device is in a moving vehicle, the other sensors will start collecting data to aid in the full functioning of the application.

Even when the program is executed and fully functioning in "active mode," it may continue to check data from the sensors to confirm that it is, in reality, in a moving vehicle (step 206). This continuous checking serves at least two purposes—it confirms that the judgment to turn on all of the sensors based on accelerometer data was accurate, and further triggers the program to turn off the sensors when the data from the sensors indicates that it is no longer in a vehicle (step 208). Upon the sensors determining collectively that the device is no longer in a vehicle (or never in fact was), the program returns to passive mode where it only draws data from the accelerometer.

The process of returning the program to passive mode may in various implementations require that the data from the sensors have determined that the device is not in a moving vehicle for some predetermined period of time. This substantially serves to prevent the program from returning to passive mode in congested traffic or other routine stops along the road.

In an alternative implementation, the process of returning the program to passive data may include a step of determining the user is in a position associated with the location of a road. This may be performed by for example using map data which has been previously downloaded to the associated device, or receiving signals from a remote server having performed the step which are representative of the user being on or off of such a position. If the determined position of a user does not coincide with a mapped road location, the process may either determine that the user is not in a moving vehicle based on the determined position alone, or may seek confirmation prior to returning to passive mode, such as for example based on the aforementioned movement data results.

The process continues in step 210 when a sound has been detected by the program as being consistent with airbag deployment in the vehicle, while the program is in active mode. The noises/impulses that the microphone detects can be interpreted in two fashions, by analyzing the sound signature (or sound signal) or by detecting the occurrence of a given threshold (measured in for example decibels—dB—as is conventionally known in the art). The more complex method of sound evaluation involves matching the sound signature collected by the microphone to that of a sampling of airbag detonation sound profiles. The more simplistic method of sound evaluation requires a threshold dB to be reached to conclude that the airbag has been deployed. Due to the extremely loud nature of airbag deployment, the noise can be uniquely identified by a threshold. Airbag deployment generates peak pressures between 167 and 173 dB which are higher than a typical mobile cellular device such as for example an iPhone can register. This means that in the event of airbag deployment the device's microphone will be saturated (for example, the current version of the iPhone's microphone saturates at 120 dB). Similar to the iPhone, most cellular phones do not contain microphones that are sensitive enough to accurately measure the pressures/impulses/noises generated by airbag deployment. This means that the microphone in the cellular device 54 can saturate when events other than an airbag deployment occur, and further explains why sound detection may desirably be used in conjunction with other data points to detect a crash.

Therefore, in step 212 the process continues by confirming the accident reading via other device sensors such as the accelerometer, in a manner which in various implementations may be substantially equivalent to that of the process 100 described above.

If the detected accident condition is not confirmed by other sensors (i.e., "no" in response to the query of step 214) the process returns to step 206. If the detected accident condition is in fact confirmed by other sensors (i.e., "yes" in response to the query of step 214) the process continues to step 216 and the program is triggered to report the accident in a manner which in various implementations may be substantially equivalent to that of the process 100 described above.

In accordance with implementations of the present disclosure as described above, the algorithm that assesses accidents may further apply a probability algorithm to maximize the efficacy of accident detection. Different values are assigned to the various sensors which are included and activated at a given time, and their respective indications. This may reduce the likelihood of accidents going undetected where not all of the sensor inputs indicate the certainty of an accident, while at the same time substantially avoiding false positives.

In another implementation, a real time feedback method in accordance with the present disclosure may deliver audible and/or visual cues to a driver after an unsafe driving maneuver has been detected. Regardless of whether the local device 10 as a cigarette lighter adapter or the mobile cellular device 54 using the computer program product is being utilized in accordance with the present disclosure, the vehicle status may include a determination of whether or not the driver is adhering to "safe" driving practices based on for example a comparison of detected vehicle speeds and/or acceleration with predetermined safety thresholds. Where a mobile cellular device 54 is used to execute the program, or is otherwise available and communicating with a local device 10, the visual cues may be displayed on the display for the device, possibly by flashing an icon or a colored screen. The audible alert, projected out over the speaker built into the handset, may generally be a safer way to cue the driver to risky driving behavior as the audible alert does not require the driver to avert their eyes from the road.

Figure 12:
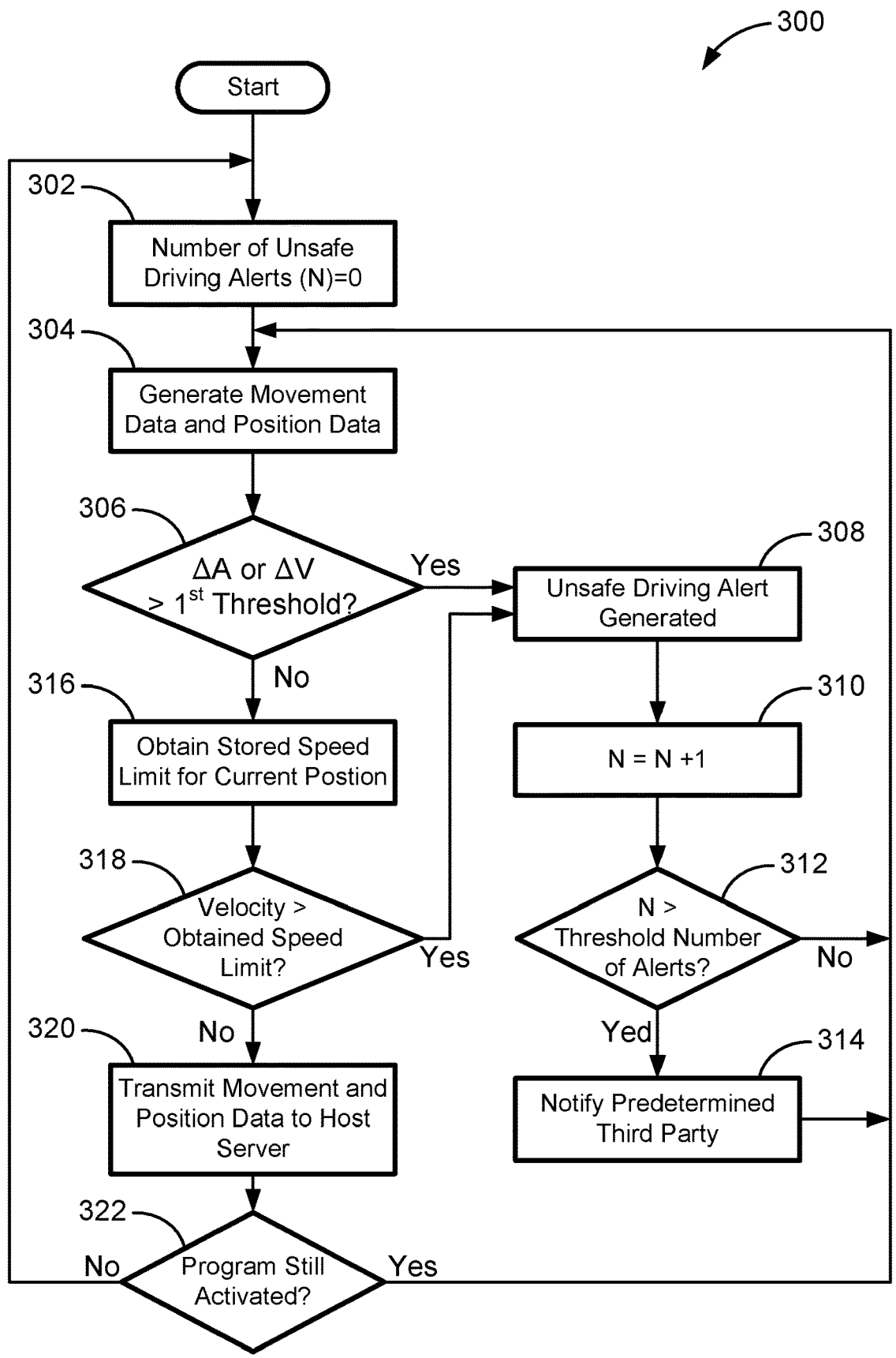
FIG. 12 is a flowchart representing an implementation of an exemplary method for real time driver feedback and third party notifications in accordance with the present disclosure.

Referring now to FIG. 12, an exemplary implementation of a real time feedback method 300 may begin when an associated local device (i.e., cigarette lighter adapter) or program product (i.e., in a mobile cellular device) is activated, powered or otherwise enabled to detect vehicle movement, at which time a number of unsafe driving alerts (N) for a particular driving session is reset to zero (step 302). The device/program then begins generating or otherwise obtaining movement data and position data associated with the vehicle in a manner substantially similar to that described above (step 304).

In step 306, the method continues by determining whether or not abrupt changes in velocity or acceleration have exceeded a predetermined threshold (safety limit). In the implementation shown, the primary sensor at work in assessing dangerous driving conditions is generally the accelerometer, as it may easily detect both abrupt increases and decreases in velocity (i.e., high magnitude acceleration or deceleration) as key indicators of unsafe driving. Alternatively or in addition, the GPS receiver may be utilized to provide safety feedback by detecting vehicle speeds.

If the change in velocity or acceleration is determined to have been greater than the predetermined threshold (i.e., "yes" in response to the query in step 306), the method proceeds to step 308 and an unsafe driving alert is generated for the benefit of the driver, which may be visually and/or audibly generated and provided as previously described. The number of unsafe driving alerts is subsequently incremented (N=N+1) in step 310 and then the new number of unsafe driving alerts is compared to predetermined threshold number of alerts (step 312). If the number of unsafe driving alerts that have been generated during a single driving session exceeds the predetermined threshold (i.e., "yes" in response to the query in step 312), the method may in various implementations proceed by generating and transmitting correspondence such as for example an email or SMS notification to a predetermined third party regarding the number of unsafe driving alerts. The email or text message may include for example the date, time, location, user name, type of unsafe driving practice (where available), number of unsafe driving alerts (N), or any of various other user-selectable options.

If the change in velocity or acceleration is determined to have been less than the predetermined threshold (i.e., "no" in response to the query in step 306), the method instead proceeds to step 316 and a stored speed limit is obtained with respect to a current position for the vehicle, as determined from the position data. The stored speed limit may be obtained from a digital map or the like which may further be stored in a remote database which is continuously accessed via a communications network, or at least relevant portions of the map may be stored in a memory on the device 10, 54. Where a speed limit is not stored for the current position, this step can obviously be skipped or omitted. Where a speed limit is available, however, the method then includes comparing the instantaneous velocity of the vehicle with the obtained speed limit for the instantaneous position (step 318) to determine if an unsafe driving event is occurring.

In various implementations, the obtained speed limit may be incremented by a predetermined "offset" or "buffer" amount which may be set as a percentage (e.g., 10%) or an absolute number (e.g., 10 MPH) such that the comparison is actually between the instantaneous velocity of the vehicle and a value corresponding to the buffered speed limit.

If the instantaneous velocity is greater than the stored speed limit, or otherwise the stored speed limit with the predetermined buffer amount applied thereto (i.e., "yes" in response to the query in step 318), the method proceeds to step 308 and continues as previously described. If the instantaneous velocity is less than the stored speed limit, or otherwise less than the stored speed limit with the predetermined buffer amount applied thereto (i.e., "no" in response to the query in step 318), the method instead moves on to step 320 and the device/program may transmit the movement data and position data to a remote server such as for example the host server as described above. In various implementations the movement data and position data may be stored locally, collected and transmitted at periodic intervals rather than continuously transmitted. Finally, the method may (in step 322) confirm that the vehicle is still in transit or otherwise that the real time feedback program is still active or enabled, consistent with the battery conservation method as previously described.

As described above, speed limit data may be obtained from a remote server and associated database. In accordance with the present disclosure, the remote database may in certain implementations include raw data which has been received or otherwise acquired from a third party such as for example the Department of Transportation (DOT). By doing this for every state a complete database of road speed limits can be acquired and used to populate a hosted or otherwise central remote database for use in real time driver feedback. The database may be considered to have substantially correct speed limits in such cases, but some of the speed limits may become outdated during the time between database updates being performed by the associated agency.

In various implementations other factors may come into play in determining unsafe driving maneuvers or circumstances. For example, the vehicle may have sensors or equivalent mechanisms for detecting conditions such as for example nighttime conditions, less-than-desirable weather conditions such as fog, rain and snow, or congested traffic conditions which might heighten the negative effects from unsafe driving. The method 300 may in such implementations be supplemented in terms of the number of steps or otherwise to modify the various thresholds in order to account for the various non-optimal driving conditions and provide alerts as appropriate.

Figure 13:
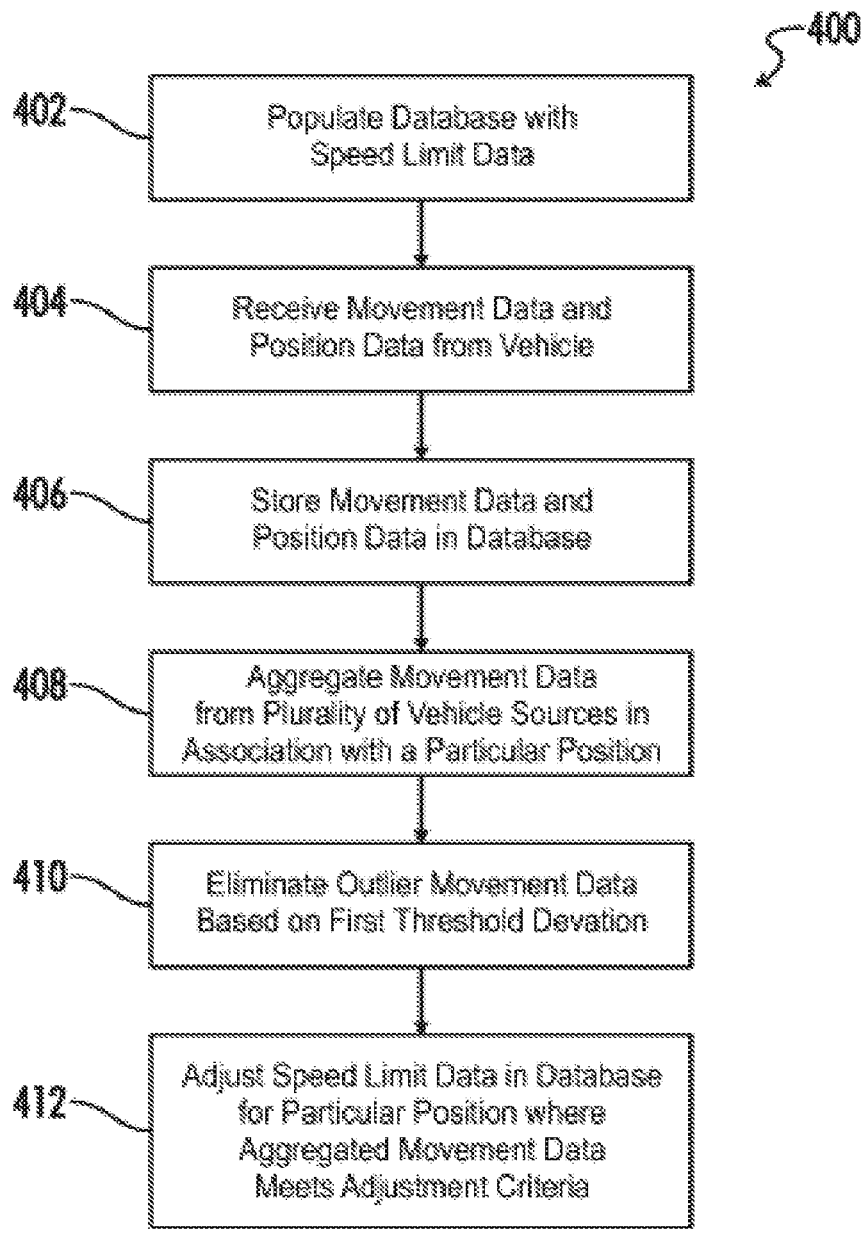
FIG. 13 is a flowchart representing an implementation of an exemplary method for automatic speed limit database updating in accordance with the present disclosure.

Referring now to FIG. 13, an exemplary speed limit data-base updating method 400 is described as may be performed by the host server of the present disclosure in accordance with device input from a number of drivers utilizing local devices 10 or cellular devices 54 running the computer program product of the present disclosure. As with other methods of the present disclosure described herein, in various implementations some of the steps may be considered optional or redundant, and the sequence in which the steps are provided may not be limiting unless a first step provides a condition precedent for continuation of the method.

The method 400 includes a first step 402 of populating the host database with speed limit data from a third party source such as for example the DOT. It may be understood that while a continuous update is preferable, this step may generally not be performed on any kind of a continuous basis, but rather in accordance with an expected update period as provided by the third party. Where the third party may for example update speed limits as they become known rather than provide periodic updates to the entire database, the host server may be programmed to request speed limit updates from the third party at predetermined intervals to encompass changes that have been made in the interim.

The host server then receives movement data and position data from a vehicle source (step 404, see also step 320 of FIG. 12) and stores the received movement data in association with a location as determined from the position data (step 406). Ideally the location may correspond to a database portion having speed limit data as populated from the third party source, such as for example a particular stretch of road including position coordinates matching those of the received position data. Where no database portion having speed limit data corresponds to position coordinates matching those of the received position data, the method may include a step (not shown) of creating a new database portion associated with a new location or otherwise uncharted road or stretch of road with respect to the latest data from the third party source.

The stored movement data may be aggregated (in step 408) with other movement data having been previously received and stored with respect to the same location or associated locations (such as an equivalent stretch of road) to generate for example an average and a median speed recorded from that particular location, while still maintaining the individual data points. In various implementations the movement data may be dated and/or other data of interest appended to the stored data entries, such that for example speed limit data from the third party source that is received on a particular date is not revised in view of vehicle data that was previously received and stored. It may be desirable to eliminate data points that are recorded as having been stored for more than a predetermined amount of time, being for example greater than the interval for updating the database with data from the third party source, which may reduce the potential effect of old readings on aggregate.

If a concentrated number of drivers in a particular area provide device input, then the host database may be updated in near real time for that particular area. This is possible because the average speed, disregarding outliers, on a given road would theoretically be consistently deviant from a posted maximum speed limit. Outliers may be eliminated or otherwise disregarded (in step 410) in accordance with a first threshold deviation value with respect to the remainder of the movement data stored in the host database for a particular location/area.

The deviation value may be determined by analyzing the aggregated movement data from the plurality of vehicle inputs with respect to a location/road with a known speed limit. If data points on a given road are found to be outside of a normal or expected range for the particular speed limit as indicated by the third party source, the host server may act by adjusting the speed limit data in the database (step 412). The determination may further include confirming that the plurality of vehicle inputs satisfy at least a threshold degree of confidence, such that for example a sufficient number of readings are available or that the number of readings are within a narrow enough band to instill a minimal degree of confidence as needed to support maximum speed limit adjustment in accordance with the present disclosure.

Recall that in describing the real time driver feedback method 300, the process included a step (316) of obtaining a stored speed limit for a current position, and the stored speed limit may be offset by a predetermined offset or buffer value which may be an absolute offset value or a percentage offset with respect to the stored speed limit. In various implementations, the local device 10 or mobile cellular device 54 running a computer program product in accordance with the present disclosure may obtain an adjusted speed limit value from the host server as derived using the speed limit database updating method 400 as further described herein. In this case, the buffer value may become redundant, as the updated speed limit value inherently represents a safe driving speed range as determined from the various data points received, stored and aggregated by the host server in association with that particular area, which accounts for the buffer value itself with respect to the underlying fixed speed limit. For example, while generally stated a road having a 55 MPH speed limit may nevertheless be safely navigated at 62 MPH in which case a buffer is desirable to prevent unsafe driving alerts at such speeds, a particular stretch of the road may have blind spots, tight curves, or the like, which would eliminate the desirability of using a buffer in such cases.

Another case where the buffer value may be considered redundant is where a process in accordance with the present disclosure is able to rely on information from a sufficient number of vehicles on a particular road in real time. In this case, real time traffic information may affect the determination of an unsafe driving alert where for example the various vehicles are traveling at a mean or median speed with a relatively small deviation (e.g., less than a predetermined deviation threshold or otherwise within an associated range based on the detected speeds and a predetermined deviation). A subsequent determination that a particular user/driver is traveling within the associated range may in such an implementation be considered to overrule an otherwise unsafe driving condition, as the driver would be permissibly traveling within the flow of traffic.

In certain implementations, a road safety mapping method may further be performed by a program executed from the host server, which may be a subset of the speed limit database updating method or otherwise independently executed. Such a method includes an algorithm for monitoring accidents and other unsafe driving events (e.g., extreme acceleration/deceleration events) as derived in accordance with methods previously described above. The events may be archived on the host server or equivalent remote central server. Overlaying the database of extreme events collected from the various users of the host system on a map using geo-coordinates, tagged to the events, generates a safety map. The safety map indicates locations where users/drivers have had accidents or otherwise generated unsafe driving alerts such as where they have been determined to have accelerated or decelerated in an extreme fashion. Knowledge of this aggregated data allows users with access to it to avoid dangerous roads or junctions when possible and to be extra alert when having to navigate them. After a large sample of data has been collected, road sections and intersections can be mapped in colors indicating their riskiness, much like traffic status is currently depicted on may global positioning systems.

In an implementation, systems and methods in accordance with the present disclosure may further be able to provide audio and/or visual alerts to a user indicating that a relatively unsafe stretch of road is upcoming or otherwise anticipated (based, e.g., on current heading, speed, alternative roads).

In an implementation, systems and methods in accordance with the present disclosure may implement a road safety mapping method as described above to determine that unsafe driving practices were used by a driver with respect to a particular stretch of road, even where not otherwise accounted for by the available speed limit data.

In an implementation, systems and methods in accordance with the present disclosure may further implement a road safety mapping method as described above to generate an optimal route between a starting point and an ending point based upon a number of criteria, which may include for example and without limitation an estimated amount of time needed to navigate each of a plurality of routes and a road safety value for each route. The road safety value may be determined by for example aggregating a number of dangerous locations along the route in accordance with predetermined weighting factors. The road safety value may further account for a number of times the driver has been recorded as previously traveling the given route, or data indicating road construction or other current road data that requires accounting.

Once a comprehensive database of road safety data is compiled insurance companies may be able to for example evaluate insurance rates taking into consideration the risk of the roads upon which the policy holder drives.

While the disclosure has been described in terms of exemplary implementations, those skilled in the art will recognize that the disclosure can be practiced with modifications in the spirit and scope of the appended claims. These examples are merely illustrative and are not meant to be an exhaustive list of all possible designs, implementations, applications or modifications of the disclosure.

What is claimed is:

1. A system comprising:
   one or more devices configured for coupling to respective vehicles and each comprising one or more sensors effective to generate output signals associated with positions and movements of the respective vehicle;
   a hosted server network communicatively linked to each of the one or more devices via a communications network; and
   a computer program product comprising one or more computer-readable memory media, the computer program product including program instructions executable by a processor to direct performance of operations further comprising:
      receiving an array of data representative of predetermined speed limit settings for an associated array of geographical locations and a driver's normal driving parameters;
      storing the array of data in a database functionally linked to the memory media and the processor;
      defining one or more unsafe driving locations in the array of geographical locations with respect to associated historical unsafe driving conditions and/or accidents and the driver's normal driving parameters; and
      for each of the respective vehicles to which one of the one or more devices are coupled,
         receiving position sensor output signals representative of vehicle position;
         receiving movement sensor output signals representative of vehicle movement;
         determining a location of the respective vehicle based on the position sensor output signals;
         determining a safe driving condition or an unsafe driving condition based on the movement sensor output signals and at least a predetermined speed limit setting associated with the location of the respective vehicle;
         aggregating data associated with vehicle movement over time with respect to corresponding locations of the respective vehicle;
         dynamically adjusting the predetermined speed limit setting associated with one or more the locations of the respective vehicle, based on the aggregated data,
         determining a potential unsafe driving condition based on the defined one or more unsafe driving locations, the driver's normal driving parameters, the determined location of the respective vehicle, and the movement sensor output signals; and
         generating an unsafe driving notification in substantially real-time in response to determining the unsafe driving condition or the potential unsafe driving condition.

2. The system of claim 1, wherein the program instructions executable to direct the performance of operations further comprising transmitting the unsafe driving notification to a remote device via a communications device functionally linked to the processor and the memory media in accordance with determined unsafe driving conditions.

3. The system of claim 2, wherein the unsafe driving notification generated in response to determining the unsafe driving condition comprises a first type of unsafe driving notification, wherein the program instructions executable by the processor to direct the performance of operations further comprising:
   aggregating an amount of the first type of unsafe driving notification generated during a particular driving session,
   comparing the aggregated amount of the first type of unsafe driving notification to a predetermined threshold value, and
   transmitting an unsafe driving notification to the remote device in accordance with the aggregated amount of the first type of unsafe driving notifications exceeding the predetermined threshold value.

4. The system of claim 3, wherein the program instructions executable by the processor to direct the performance of operations further comprises determining the safe driving condition or the unsafe driving condition based on the movement sensor output signals, the predetermined speed limit setting associated with the location of the respective vehicle, and a predetermined absolute offset value with respect to various speed limit settings.

5. The system of claim 3, wherein the program instructions executable by the processor to direct the performance of operations further comprises determining the safe driving condition or the unsafe driving condition based on the movement sensor output signals, the predetermined speed limit setting associated with the location of the respective vehicle, and a predetermined percentage offset value with respect to various speed limit settings.

6. The system of claim 1, wherein the program instructions executable by the processor to direct the performance of operations further comprising:
   determining a change in movement by the respective vehicle from the movement sensor output signals,
   comparing the determined change in movement by the respective vehicle to a rate of change threshold value, and
   determining the unsafe driving condition based on the determined change in movement by the respective vehicle exceeding the rate of change threshold value.

7. The system of claim 1, wherein the operation of dynamically adjusting the speed limit setting comprising disregarding vehicle movement data for respective vehicle locations outside of a threshold deviation value, and adjusting the speed limit settings based on one or more of a determined average speed and a determined median speed from remaining vehicle movement data.

8. The system of claim 1, wherein at least one of the one or more devices comprises a cigarette lighter plug or 12 volte outlet configured to engage a cigarette lighter socket as a power source associated with a respective vehicle, the at least one device positioned in a fixed manner relative to the respective vehicle when coupled thereto.

9. The system of claim 1, wherein at least one of the one or more devices further comprises:
- a first portion comprising a cigarette lighter plug configured on a first end for coupling to a cigarette lighter socket and positioned in a fixed manner relative to the respective vehicle when coupled thereto;
- a second portion coupled to a second end of the first portion and moveable between a first position and a second position; and
- a locking mechanism effective to permit movement by the second portion relative to the first portion in a first state and to prevent movement by the second portion relative to the first portion in a second state.

10. The system of claim 1, wherein at least one of the one or more devices further comprises an audio sensor, and wherein the program instructions further executable to receive audio output signals from the audio sensor and to determine a movement status associated with an accident based on the movement sensor output signals, the audio sensor output signals and one or more accident threshold settings.

* * * * *